United States Patent [19]

Newton et al.

[11] Patent Number: 5,688,269

[45] Date of Patent: *Nov. 18, 1997

[54] ELECTROSURGICAL APPARATUS FOR LAPAROSCOPIC AND LIKE PROCEDURES

[75] Inventors: David W. Newton, Boulder; Roger C. Odell, Louisville; Don R. Boyle, Boulder, all of Colo.; James Richard Gannoe, Southbridge; John J. Laviolette, Palmer, both of Mass.

[73] Assignee: Electroscope, Inc., Boulder, Colo.

[*] Notice: The term of this patent shall not extend beyond the expiration date of Pat. No. 5,312,401.

[21] Appl. No.: 38,104

[22] Filed: Mar. 30, 1993

Related U.S. Application Data

[63] Continuation-in-part of Ser. No. 727,946, Jul. 10, 1991, Pat. No. 5,312,401.

[51] Int. Cl.⁶ ................................................ A61B 17/39
[52] U.S. Cl. ............................ 606/46; 606/35; 606/42
[58] Field of Search ........................... 606/32–35, 37–42, 606/44–47

[56] References Cited

U.S. PATENT DOCUMENTS

| | | | |
|---|---|---|---|
| 2,004,559 | 6/1935 | Wappler et al. | 606/46 |
| 3,601,126 | 8/1971 | Estes . | |
| 3,706,008 | 12/1972 | Kremer . | |
| 3,707,149 | 12/1972 | Hao et al. | 606/32 |
| 3,804,096 | 4/1974 | Gonser . | |
| 3,838,242 | 9/1974 | Goucher . | |
| 3,895,635 | 7/1975 | Justus et al. | 606/35 |
| 3,898,991 | 8/1975 | Ikuno et al. . | |
| 3,905,373 | 9/1975 | Gonser . | |
| 3,913,583 | 10/1975 | Bross . | |
| 3,933,157 | 1/1976 | Bjurwill et al. . | |
| 3,946,738 | 3/1976 | Newton et al. . | |
| 4,181,131 | 1/1980 | Ogiu . | |
| 4,184,492 | 1/1980 | Meinke et al. . | |
| 4,200,104 | 4/1980 | Harris . | |
| 4,231,372 | 11/1980 | Newton . | |
| 4,237,887 | 12/1980 | Gonser | 606/35 |
| 4,303,073 | 12/1981 | Archibald | 606/35 |
| 4,325,374 | 4/1982 | Komiya . | |
| 4,343,308 | 8/1982 | Gross | 606/35 |
| 4,374,517 | 2/1983 | Hagiwara . | |
| 4,449,532 | 5/1984 | Story | 606/191 |
| 4,494,541 | 1/1985 | Archibald | 606/32 |
| 4,615,330 | 10/1986 | Nagasaki et al. | 606/42 |
| 4,617,927 | 10/1986 | Manes | 606/38 |

(List continued on next page.)

FOREIGN PATENT DOCUMENTS

| | | | |
|---|---|---|---|
| 1139927 | 8/1961 | Germany . | |
| 3013784 | 10/1980 | Germany | 606/46 |
| 53-13583 | 2/1978 | Japan . | |

*Primary Examiner*—David M. Shay
*Attorney, Agent, or Firm*—Sixbey, Friedman, Leedom & Ferguson, P.C.; Gerald J. Ferguson, Jr.

[57] ABSTRACT

A safety shield for use in laparoscopic or like electrosurgical procedures where the shield surrounds the active electrode and extends from a trocar or the like to the field of view of the surgical procedure. The shield is connected to the return lead via a low impedance path which includes monitor circuitry for determining whether the shield current is associated with an abnormal condition. The shield may also serve as a structural element of the instrument and be connected to the instrument body so that the instrument is maintained at or near patient potential. Moreover, a unitary connector is provided whereby connection to the active electrode and shield may be made by a single connector. Attached to the connector is a cable in which both the active and shield conductors are contained for at least a distance sufficient to minimize clutter in the operative site. Articulatable instruments incorporating the above features are also disclosed where different implementations are utilized to absorb the longitudinal reactive forces generated upon articulation of the tips. An adjustable insulating sheath for use with the articulatable instruments is also utilized so that the tips can be exposed more or less depending upon the particular surgical application.

61 Claims, 19 Drawing Sheets

U.S. PATENT DOCUMENTS

| | | | |
|---|---|---|---|
| 4,618,885 | 10/1986 | Nagasaki | 606/46 |
| 4,638,802 | 1/1987 | Okada. | |
| 4,662,369 | 5/1987 | Ensslin. | |
| 4,716,897 | 1/1988 | Noguchi et al.. | |
| 4,844,063 | 7/1989 | Clark | 606/37 |
| 4,919,129 | 4/1990 | Weber, Jr. et al. | 606/49 |
| 5,007,257 | 4/1991 | Farrin et al. | 606/35 |
| 5,312,401 | 5/1994 | Newton et al. | 606/35 |

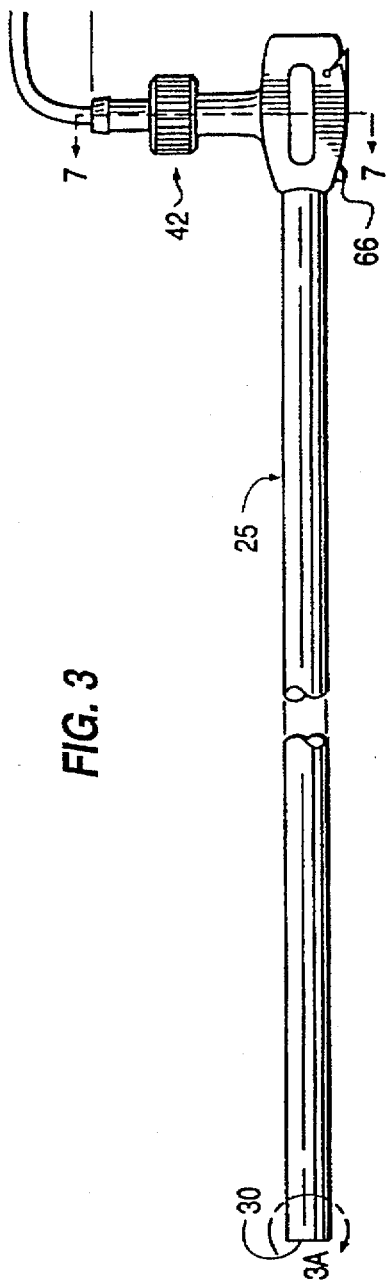
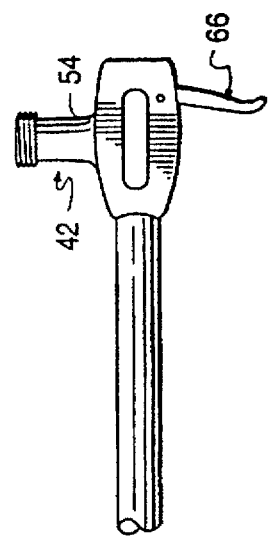
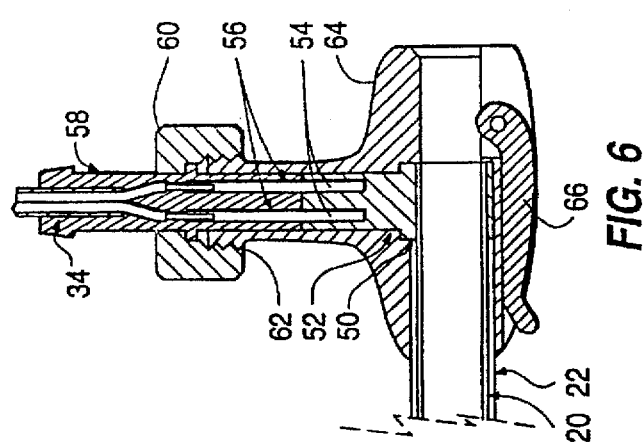
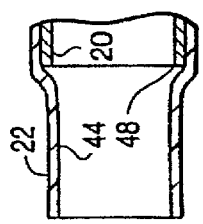
FIG. 3
FIG. 3A
FIG. 5
FIG. 6

ELECTROSURGICAL APPARATUS FOR LAPAROSCOPIC AND LIKE PROCEDURES

RELATED APPLICATION

This application is a Continuation-In-Part of application Ser. No. 07/727,946 filed Jul. 10, 1991 now U.S. Pat. No. 5,312,401.

BACKGROUND OF THE INVENTION

This invention is related to electrosurgical apparatus and in particular to such apparatus for performing laparoscopic, pelviscopic, athroscopic, thoroscopic and like procedures.

Procedures of the foregoing type are experiencing explosive growth in that incisions are kept to a minimum size and thus such procedures facilitate shorter hospital stays and lower costs. For example, with laparoscopic surgery, a patient can return to normal activity within about one week, whereas with procedures where a large incision is made, about a month for full recovery may be required.

It is to be understood that hereinafter and in the claims, whenever the term "laparoscopic" is employed, similar procedures such as pelviscopic, athroscopic, thoroscopic, and the like where small incisions of the foregoing type are made are also encompassed by this term.

Referring to FIG. 1, there is illustrated a prior art electrosurgical laparoscopic apparatus including a trocar sheath or cannula 10 which is conventionally used to provide a conduit through a patient's skin into the peritoneal cavity. Removably insertable through the trocar sheath is an active electrode probe 12 which includes an electrode 14 and an insulative coating 16 thereon. The tip 18 of the probe may be of different conventional shapes such as needle-shape, hook-shape, spatula-shape, graspers, scissors, etc. and serve various conventional functions such as suction, coagulation, irrigation, pressurized gas, cutting, etc. There are various problems which may arise with respect to the use of the prior art apparatus when used in laparoscopic or like procedures.

A first problem may arise if the insulation 16 on the active electrode is damaged thereby allowing the active current (possibly in the form of arcing) to pass therethrough directly to the patient's tissue (possibly the bowel or colon) whereby peritonitis may set in within several days. The arcing may occur out of the surgeon's field of view which may extend as little as about 2 centimeters from the tip of the active electrode (or the surgical field). The field of view is typically established by illumination and viewing sources inserted through one or more other trocar sheaths at other incisions.

Out of the field of view, there can be many centimeters of insulated active electrode which extend between the trocar sheath and the field of view. This area which is out of the field of view is potentially dangerous. Here, the insulated active electrode may come into contact with the bowel in procedures where the gall bladder, for example, is removed. If the damaged insulation and thus the attendant arcing were to occur within the field of view, the surgeon normally would immediately observe this and deactivate the generator. However, the damaged insulation can and more probably will occur at a site removed from the field of view and thus the surgeon will not be able to observe the arcing which is occurring at the bowel. Furthermore, due to the repeated insertion of the active electrode probe through the trocar sheath, the insulation thereon can be damaged especially since this accessory is quite often pushed through the trocar sheath rather roughly. Hence, damage to the active electrode insulation is particularly a problem in that the full active current may pass through the area of damaged insulation to the return electrode via an unintended site such as the bowel.

A second problem which can arise with the prior art device of FIG. 1 is caused by a capacitive effect where one electrode of the capacitance is the active electrode and the other electrode of the capacitance is the metallic trocar sheath and the dielectric between these elements is the insulation on the active electrode, as can be seen in FIG. 1. Current from the active electrode will be capacitively coupled to the trocar sheath and then returned through the body and the return electrode to the generator. If this current becomes concentrated, for example, between the trocar sheath and an organ such as the bowel, the capacitive current can cause a burn to the organ.

A third potential problem occurs if the active electrode contacts another instrument within the peritoneal cavity such as metallic grippers or the like. The above-mentioned capacitive effect also arises in this situation where the first electrode is the active electrode and the second electrode is the metallic graspers or the like. Thus, where the grippers contact a unintended site, injury may occur.

SUMMARY OF THE INVENTION AND DISCUSSION OF PRIOR ART

To render laparoscopic electrosurgical procedures more safe and thus overcome the above-mentioned problems, the present invention provides a tubular, insulated, conductive safety shield which extends at least from the trocar sheath to the field of view (that is, typically within less than two centimeters from the active electrode tip). This provides the protection which is needed with respect to the above-discussed first problem where arcing may occur at an unintended site out of the field of view. In particular, the insulated shield may be first inserted through the trocar sheath and then the active electrode inserted through the insulated shield although the order is not important. Thus, the active electrode may be assembled to the shield before insertion of the shield and active electrode through the trocar sheath.

The insulation is provided at least on the outer surface of the shield and is preferably also provided on the inner surface of the shield. The purpose of the insulation on the outer surface is to insure that the shield is insulated from the trocar sheath and to prevent the shield from becoming an unintended return electrode. One purpose of the insulation at the inner surface of the shield is to provide an additional layer of insulation if the insulation on the active electrode fails.

Assuming the insulation on the active electrode is damaged, current will pass through the damaged insulation to the shield and then be returned to the return lead via a low impedance electrical connection between the shield and the return lead of the electrosurgical generator where the impedance should be less than about 20 ohms. A monitor circuit responsive to the shield current preferably deactivates the electrosurgical generator whenever the shield current corresponds to an abnormal condition such as an insulation breakdown.

The insulated shield of the present invention also addresses the second and third above-mentioned problems by harmlessly returning any current which is capacitively coupled to the shield to the return lead via the above-mentioned low impedance connection.

U.S. Pat. No. 4,184,492 to H. Meinke et al. discloses an electrosurgical resectoscope wherein insulation may be provided on the outer surface of an instrument body and where the instrument body may be connected to the return lead via a monitor circuit. However, this apparatus is not concerned with providing protection between the instrument body and the field of view. Furthermore, there is no suggestion of a safety shield in Meinke et al. and, in particular, a safety shield which extends between a trocar sheath and the field of view. Moreover, the Meinke et al. resectoscope is prone to undesired capacitive coupling to other instruments. Moreover, the monitor circuit of Meinke et al. is not sensitive to spectral components or phase aspects of the sensed current in a trocar sheath whereas such parameters of the sensed shield current are important in the present invention with respect to the detection of active electrode insulation breakdown, as will be described in more detail hereinafter.

The monitoring circuitry of the present invention may be integral with the electrosurgical generator or may be separate from it and attached as an outboard module. In general, the safety shields of the present invention may be used in laparoscopic, pelvistopic, atheroscopic, thoroscopic, and other procedures where punctures are made in the patient's skin. The shields may be part of an active accessory or they may be separate and used over existing accessories. The accessories are intended for use with insulating or conductive trocar sheaths which form a conduit through the skin.

As stated above, insulation is provided at least on the outer surface of the shield principally to prevent the shield from becoming a parallel return electrode. The shield may also have redundant internal insulation to add to the accessory insulation. Moreover, the insulation at the shield tip is designed to prevent surface conduction from the active electrode to the shield tip.

The monitor circuitry may evaluate various parameters of the shield current to determine whether an abnormal condition such as active electrode insulation breakdown has occurred. Thus, the phase of the active current or voltage may be measured with respect to that of the shield current or voltage. Alternatively, or in addition to, a predetermined spectral content of the shield current may be analyzed. Further, relative amplitudes of the sensed shield current and the generator return current may be compared whereby a threshold ratio may be defined which indicates a hazard. Moreover, the shield current may be compared with an absolute limit to provide a fault condition indication.

Furthermore, the outputs of the measurements described above may be combined so that individual measurement results not sufficient to produce an alert may be evaluated together to produce such an alert.

Moreover, the connection of the shield is redundant and monitored by providing a small sensing current through the pair of conductors connected to the shield. If the circuit to and from the shield is not complete, a fault condition is sensed.

The results of the measurements of shield current flow may be presented in digital or analog form. These results may then be recorded on a computer or chart recorder for future reference.

The safety shield may also be used with hand pieces used to perform tonsillectomies and the like.

Since any insulation can become damaged, a disposable (limited use) shield with a complete insulation system may also be used with uninsulated instruments so that all insulation is replaced with each use. This embodiment enhances cleanability since the reusable instrument has little, if any, interface with the insulation.

Means may also be provided to adjustably position the tip of the active probe as desired by the user with respect to the distal end of the shield and then latch the active probe in place at the desired position. The adjustability feature is advantageous for several masons including providing a capability whereby the tip exposure can be adjustably limited.

Means may further be provided to prevent the shield from becoming a return electrode by requiting the use of a dual-area return electrode. Thus, the monitor may employ an industry standard connector, which is used to monitor return electrodes. This connector uses a pin to designate a dual area electrode and the monitor of the present invention may have a switch activated by that pin. A fault condition is presented if use is attempted without the dual-area return electrode as represented by the pin. Moreover, by providing insulation on the inner and outer surfaces of the shield, this also prevents the shield from becoming a return electrode.

In another embodiment of the invention, a tubular insulative member is removably insertable through the trocar sheath and includes an elongated port through which irrigation fluid or suction or gas may pass. The active electrode probe is attached to the end of the tubular member where the electrical connection thereto extends through the insulated portion of the tubular member and where a tubular conductive shield surrounding the electrical conductor is also disposed within the insulated portion of the tubular member.

As described above, the various embodiments incorporate an electrical safety shield around monopolar active conductors to provide improved safety. The shielding technology prevents stray capacitive coupling and also provides a fail-safe condition if active conductor insulation breaks down. In many applications it is desirable to incorporate the shield technology around conventional active instruments. However, certain shortcomings may arise when the foregoing is implemented.

For example, most conventional accessories are 5 mm in diameter and the incorporation of a shield typically increases this value to approximately 7.5 mm diameter. Often this is not a problem since a 10 mm cannula is employed and a reducer can be included to accommodate 7.5 mm. However, where other 5 mm instruments are being used interchangeably, the 7.5 mm value can sometimes be considered as a problem.

Accordingly, in accordance with a further primary object of the invention, novel electrosurgical instruments are provided in accordance with the present invention wherein the above discussed shield is integrated with the active accessory such that the total diameter thereof can be reduced to 5 mm, for example, for certain instruments where the shield conductive tube becomes a principle structural element of the accessory.

Moreover, in accordance with a further object of the invention, the (a) instrument body including the handle manipulated by the surgeon and (b) safety shield of the integrated accessory of the present invention are maintained an electrical potential which is close to the patient potential that is, the impedance between (a) the instrument body and the shield and (b) the return lead of the electrosurgical generator should be less than about 20 ohms and/or the voltage on the instrument body and the shield should be less than about thirty volts. Thus, certain problems associated with conventional active accessories are overcome in that such accessories are usually maintained at the active potential and provided with an insulating coating to protect the surgeon. However, this coating can become damaged and without any warning, the result can be a burn to the surgeon's hand. In the present invention there is no need to insulate the parts of the instrument and, in particular, the handle manipulated by the surgeon inasmuch as instrument parts are maintained at or near patent potential.

A further advantage of present integrated active/shield instrument of the present invention is that the amount of time spent in set up can be reduced since it is not first necessary to assemble the shield through a trocar cannula or the like and then insert the active accessory through the shield. Rather, both the shield and the active electrode are inserted through the cannula in a single step since the shield and active are integrated into a single instrument.

As stated above, the body of the instrument is maintained at essentially patient potential in accordance with a primary object of the invention. This feature may be incorporated both in non-articulating and articulating instruments. Moreover, different implementations of articulating implements are also employed which incorporate the foregoing feature of maintaining the instrument body at or near patient potential.

Furthermore, conventional active accessories typically connect to the active cord with a banana receptacle as part of the cord and a banana pin as part of the accessory. Typically there is a gap in the insulation between the cord and the accessory and this gap can result in a discharge of current particularly is moisture is present in the gap.

Accordingly, it is a further object of the present invention to provide an improved connector to the above integrated electrosurgical instrument wherein the possibility of such a discharge occurring at the connection point between the instrument and the active cord is substantially eliminated.

As discussed above, many of the embodiments described hereinbefore are directed to the incorporation of a shield product around conventional active instruments where the shield and the active instruments are separate products. However, as also discussed above, in accordance with a further feature of this invention, the shield and the active accessory are integrated into a single instrument. Moreover, in accordance with yet a further feature of the invention, an improved connector is provided which allows the connection to the electrosurgical active electrode and the shield conductors in a one piece connector assembly. Thus, it is not necessary for the surgeon to make two connections to the active accessory which may be more time consuming than desired. Rather, by making a single connection to the active accessory, connections are made both to the active electrode and to the shield conductors with the integrated, one piece connector assembly.

These and other objects of the invention will become apparent from a reading of the following specification and claims taken with the drawings.

BRIEF DESCRIPTION OF THE DRAWINGS

FIG. 3 is a side view of the laparoscopic apparatus of FIG. 2.

FIG. 3A is a cross-sectional view of an enlarged end portion of the apparatus of FIG. 3, FIG. 5 is aside view of the apparatus of FIG. 3 with the latch thereof in its release position.

FIG. 6 is a cross-sectional view taken along the line 6—6 of FIG. 4 which illustrates in detail an illustrative electrical connector to the shield.

DETAILED DESCRIPTION OF PREFERRED EMBODIMENTS

Figure 1:
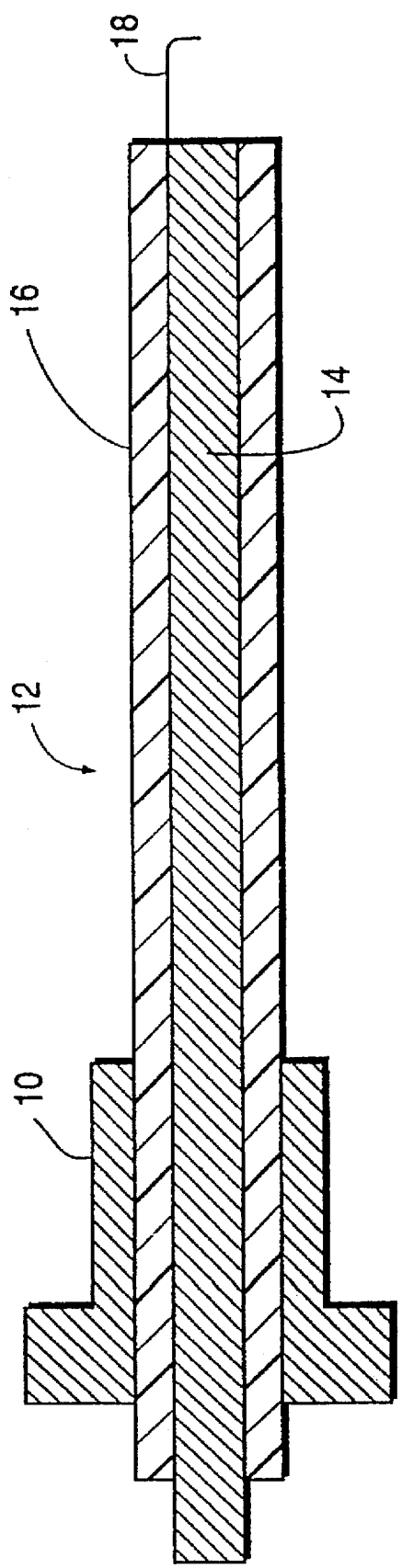
FIG. 1 is across-semifinal view of a prior art laparoscopic electrosurgical apparatus.
Figure 2:
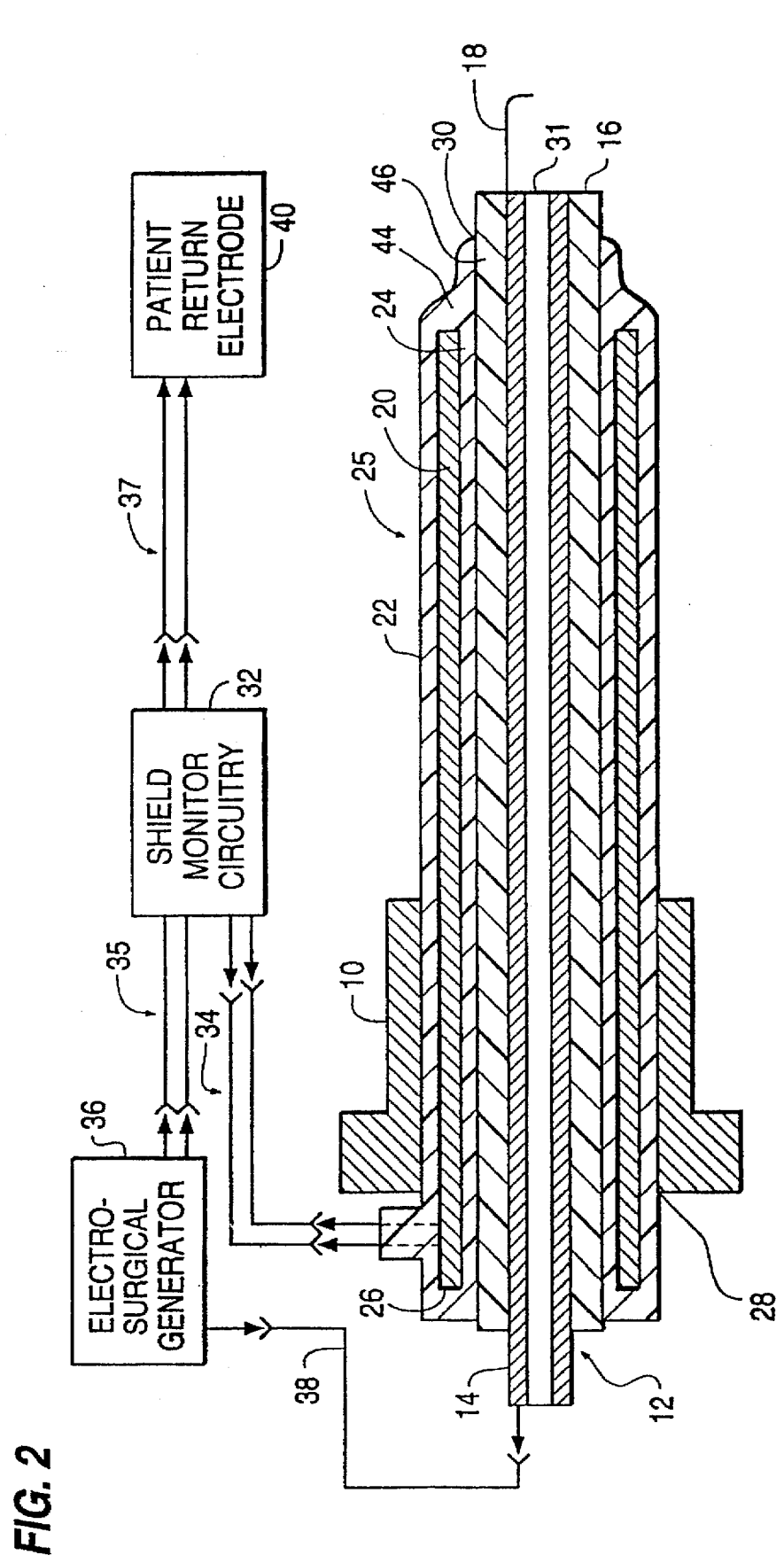
FIG. 2 is a cross-sectional view of an illustrative laparoscopic apparatus in accordance with the present invention.
Figure 4:
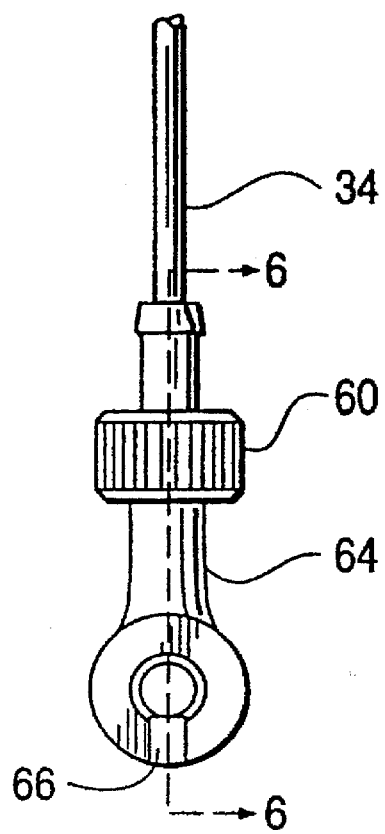
FIG. 4 is an end view of the laparoscopic apparatus of FIG. 3.
Figure 7:
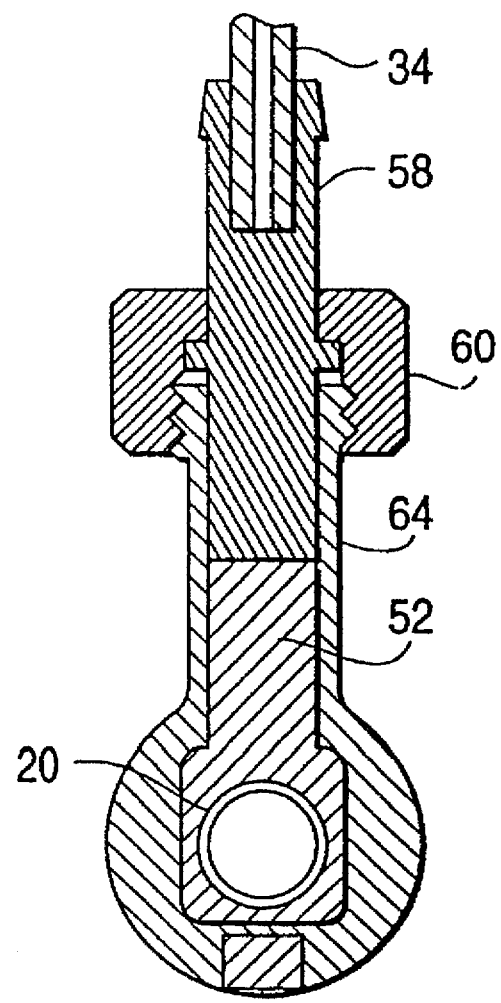
FIG. 7 is a cross-sectional view taken along the line 7—7 of FIG. 3 which further illustrates the electrical connector of FIG. 6.

Referring to the drawing where like reference numerals refer to like parts, there is illustrated in FIG. 2 an illustrative laparoscopic electrosurgical apparatus in accordance with the present invention. A tubular safety shield assembly 25 includes a tubular shield 20 having a layer of insulation 22 provided on the outer surface thereof and an optional layer of insulation 24 provided on the inner surface thereof. The tubular shield assembly is inserted through trocar sheath 10 to thereby provide a passageway through which the active electrode probe 12 may be inserted. An elongated port 31 may extend through the active electrode through which irrigation fluids, suction, a pressurized gas stream, etc. may pass. When active probe 12 and tubular shield assembly 25 are in their respective inserted positions as shown in FIG. 2, the shield 20 surrounds the active probe from at least (a) a proximal point 26 prior to the entry point 28 of the active probe into the trocar sheath 10 to (b) a distal point 30 in proximity to the tip 18 of the active probe.

Shield monitor circuitry 32 is connected to shield 20 via a dual conductor lead 34 whereby the integrity of the connection of the shield to the monitor circuitry can be monitored.

The active electrode probe 12 is connected to an electrosurgical generator 36 which may be of a conventional type via an active lead 38. The electrosurgical generator is connected to a patient return electrode 40, which preferably should be of the dual area type, via the shield monitor circuitry 32 and, in particular, the return terminal of the generator is connected to circuitry 32 via lead 35 while the circuitry 32 is connected to the return electrode via lead 37. As will be described hereinafter, upon detection of a fault condition by the shield monitor circuitry, the electrosurgical generator 36 may be deactivated by opening a relay in the connection between the generator and patient return electrode 40 although other means may also be employed to deactivate the generator.

Referring to FIGS. 3 through 7, there is illustrated the shield assembly 25 including shield connector assembly 42. In the FIG. 3 embodiment, insulation 22 is provided only on the outer surface of shield 20 as can be seen in FIG. 3A, which is an enlarged cross-sectional view of the distal end 30 of the shield assembly 25. Thus, there is no inner insulation layer in FIG. 3A corresponding to inner insulation layer 24 of FIG. 2. The portion 44 of insulating layer 22 extending beyond sleeve 20 is preferably of reduced inner diameter so that when the active electrode probe is inserted through the shield assembly 25, a tight connection will result between the active probe and portion 44 as illustrated in FIG. 2 at 46 and FIG. 3A at 44. Hence, the insulation portion 44 at the shield tip prevents surface conduction from active electrode tip 18 to the distal end 48 of shield 20. The reduced diameter portion 44 may be effected by heat shrinking or other appropriate techniques.

Referring to FIG. 6, the shield tube 20 is press fit at 50 to a connector element 52. Connector 52 has two pin receptacles 54 adapted to receive the pins 56 of a plug 58 attached to dual lead 34 of FIG. 2. The plug 58 is removably secured to connector 52 via a thumb wheel 60 threaded onto a threaded portion 62 of an insulating portion 64 which surrounds connector 50 and which is also illustrated in FIG. 5.

As can be seen in FIG. 6 when the plug 58 is properly inserted into connector 52 an electrical path is established between the pins 56 through the connector. As will be discussed hereinafter with respect to the monitor circuitry, it is this electrical connection which is monitored to insure that dual lead 34 is properly connected to shield tube 20.

A latch 66, one example of which is shown in FIGS. 5 and 6, is preferably employed to secure the active probe in place after it has been inserted through the shield accessory 25, the latch being shown in its secured position in FIG. 6 and in its release position in FIG. 5. Other means may also be employed to releasably secure the active probe in place including a compression collet type lock. Note the tip of active probe may be positioned as desired by the user with respect to the distal end of shield accessory 25 before the latch is operated to latch the active probe in place with respect to the shield accessory. This adjustability feature is advantageous in that different accessories have different needs for the close spacing of the insulation with respect to the tip. Moreover, different surgeons may have different preferences with regard to their fields of view which is a variable. Furthermore, this feature may be utilized to adjustably limit the tip exposure.

Figure 8:
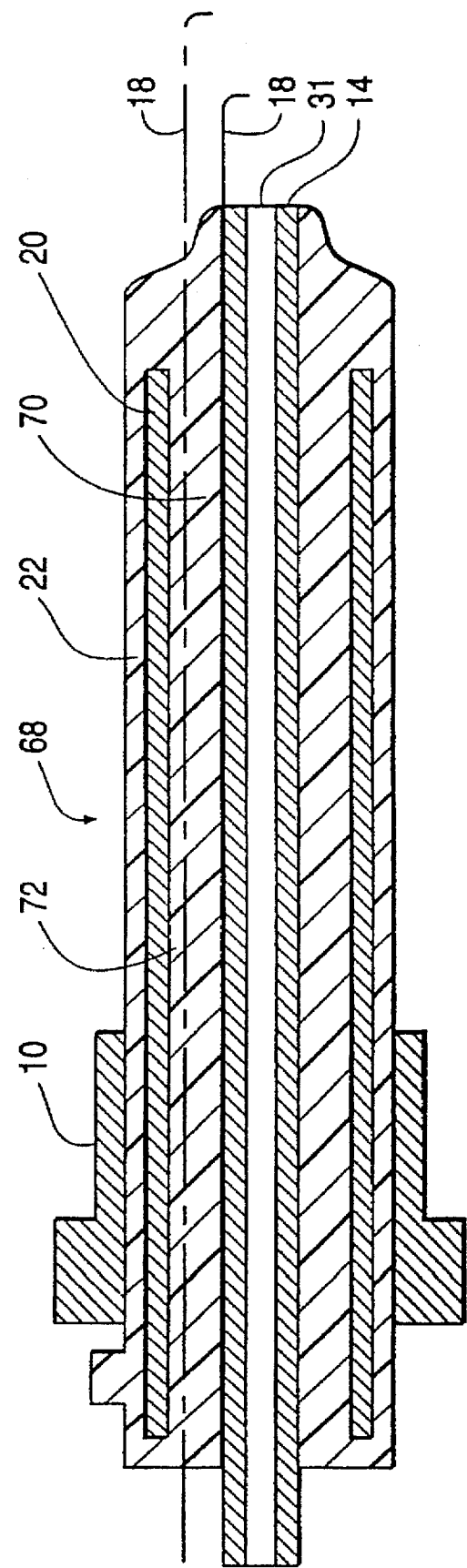
FIG. 8 a cross-sectional view of a further embodiment of a laparoscopic electrosurgical apparatus in accordance with the present invention.

Referring to FIG. 8, there is shown a further embodiment of the invention where there is no (or minimal) insulation on active electrode 14. Extending through the active electrode is elongated port 31 through which irrigation fluids, suction, pressurized gas, etc. may pass. Moreover, port 31 may be utilized for various further functions such as gas-augmented-fulguration, a specialized field in which the safety shield of the present invention appears to be particularly advantageous. The safety shield assembly 68 includes shield 20 with insulation layer 22 on the outer surface thereof and insulation layer 70 on the inner surface thereof. Thus, insulation layer 70 provides the insulation between shield 20 and active electrode 14. Shield 68 is disposable (limited use) and as can be appreciated from the foregoing provides a complete insulation system which can be used with uninsulated trocar sheath 10 and uninsulated active electrode 14. Hence, since shield 22 is disposable (limited use), all insulation is replaced with each use or after a limited number of such uses. This embodiment also enhances cleanability since the reusable instrument does not have a permanent interface with the insulation. In this embodiment although no insulation is shown on active electrode 14 there may be a small mount if so desired.

In another embodiment of the invention as also illustrated in FIG. 8, the tubular electrode 14 may be eliminated and the active electrode extended through the insulating layer 70 as a conductor 72 as indicated by the phantom line where tip 18 is attached to the distal end of the conductor. This embodiment is advantageous in that the port 31 extending through sleeve assembly 68 may have its diameter widened to the outer diameter of removed electrode 14. Moreover, the number of separate parts is reduced to one with the elimination of removable electrode 14 and the incorporation of the conductor 72 within insulating portion 70.

Figure 9:
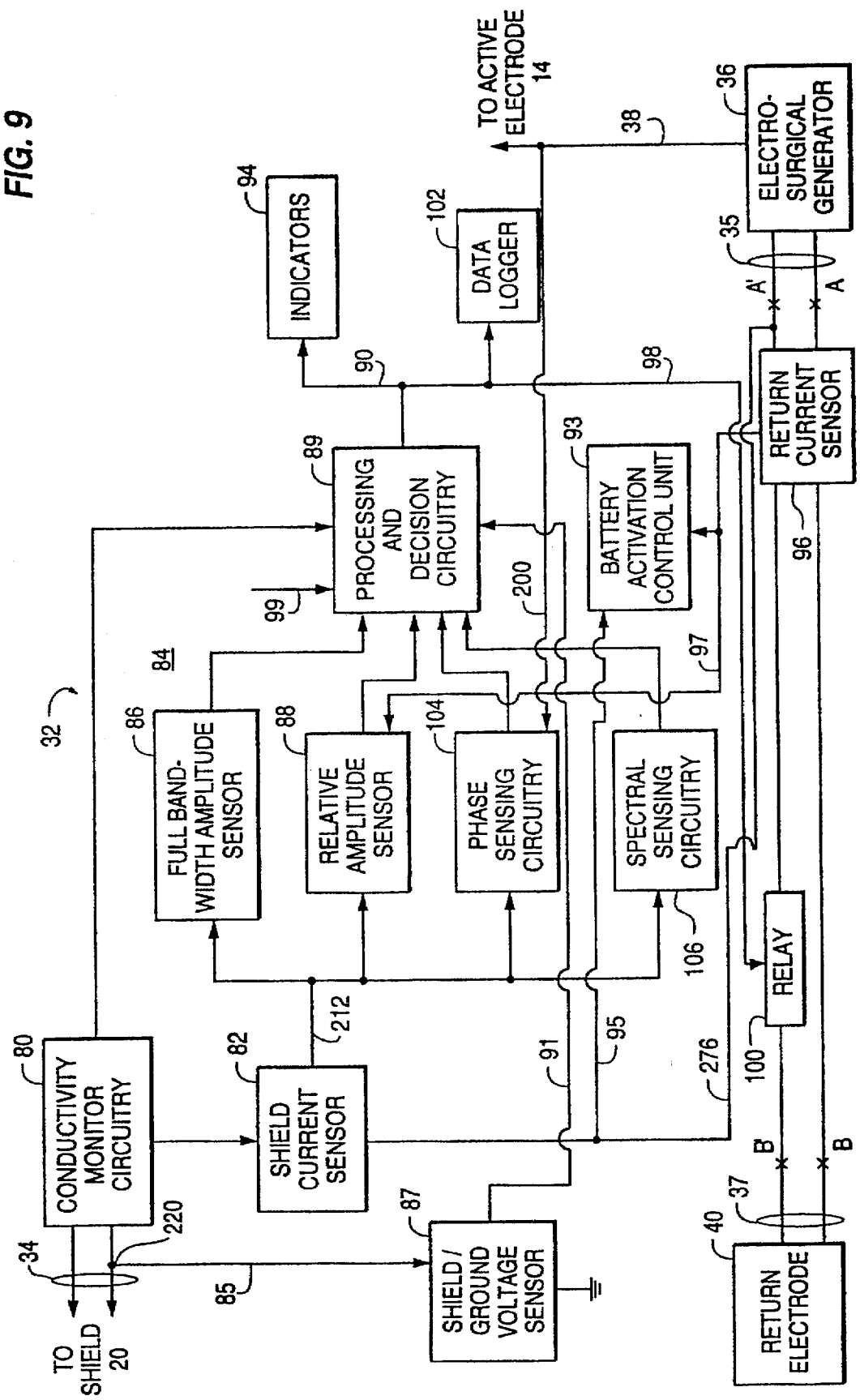
FIG. 9 is a generalized block diagram of illustrative monitor circuitry for use in the present invention.

Referring to FIG. 9, there is illustrated a generalized block diagram of the shield monitor circuitry 32 of FIG. 2. In particular, a conductivity monitor 80 is connected to dual lead 34, the purpose of the conductivity monitor circuit being to measure the integrity of the connection of lead 34 to shield 20. The dual connection provides a redundant path for shield monitoring current which is applied to lead 34 as will be described in more detail hereinafter with respect to FIG. 10.

A shield current sensor 82 senses the current passing from the shield 20 to return electrode lead 35, 37. The shield current sensor may provide a signal voltage proportional to the instantaneous value of the shield current as will be explained in more detail with respect to FIG. 10.

Measurement electronics circuitry 84 includes various circuits for measuring different parameters of at least the sensed shield current. The first of these circuits is a full bandwidth amplitude sensor 86 which measures the amplitude of the full bandwidth of the sensed shield current. A processing and decision circuit 89 determines whether this amplitude exceeds a predetermined threshold and if it does, a fault condition may be applied to indicators 94 over line 90. Indicators 94 may be aural and/or visible and provide an appropriate alert.

In addition to applying an alert signal over line 90, a generator deactivate signal is applied over line 98 to a relay 100 which opens the connection between return electrode 40 and generator 36 to thus deactivate the generator and discontinue the application of electrosurgical energy.

That is, the monitor circuitry 32, when used outside host electrosurgical generator 36 (as illustrated in FIG. 2), is preferably used with an electrosurgical generator of the type having a dual return electrode lead whereby the integrity of the return electrode connection can be monitored. Such monitoring circuitry is known whereby a split (or double) patient electrode is employed and a DC current (see German Patent No. 1139927 published Nov. 22, 1962) or an AC current (see U.S. Pat. Nos. 3,933,157 and 4,200,104) is passed between the split electrodes to sense patient contact resistance or impedance between the patient and the electrodes. If an open circuit condition is sensed, the generator is deactivated. Since the relay 100 of FIG. 9 is opened upon detection of a fault condition, the return electrode connection is also opened to thus deactivate the generator. However, it is to be understood other means will also occur to those skilled in this art for deactivating the generator upon detection of a fault condition by monitor circuitry 32.

A data logger 102 may also be connected to processing and decision circuitry 89 to provide a hard copy of various safety conditions.

Relative amplitude measurement circuitry 88 may be responsive to the ratio of the amplitudes of the sensed shield current and the sensed return electrode current as determined by return current sensor 96. Processing and decision circuitry 89 determines whether this ratio exceeds a predetermined threshold and if it does an alert signal is applied over line 90 while a deactivate signal is applied over line 98 to relay 100 in a manner similar to that described above with respect to the absolute amplitude fault condition.

Phase sensing circuitry 104 is responsive to the phase difference between the voltage applied to the active lead 38 of FIG. 2 and the sensed shield current. In FIG. 2 the monitor circuitry 32 is indicated as being housed outside host electrosurgical unit 36. However, it may also be incorporated within the electrosurgical generator. In the latter instance, access may be readily gained to the active voltage and thus the phase comparison made by phase sensing circuitry 104 can be readily effected. When the monitor is located outside of the host electrosurgical unit, it is somewhat more inconvenient to gain access to the applied voltage signal; nonetheless, appropriate means will occur to those of ordinary skill in the art to gain access to this signal.

Detection of the phase difference between the active voltage and the shield current is a particularly good indicator of a fault condition. That is, normal shield currents are exclusively capacitive—in particular, due to the capacitive coupling between active electrode 16 and shield 20, there is a 90' phase difference between the active voltage and the shield current under normal conditions. Hence, as long as the insulation between the active electrode and the shield is intact, a normal condition will be sensed by phase sensing circuitry 104 where the phase circuitry may be of the type shown in FIG. 11 as will be described in more detail hereinafter.

In general, the phase sensing circuitry, in response to the phase difference between the applied inputs being 90', provides a first output (high voltage, for example). If there is an insulation breakdown between the active electrode 16 and the safety shield 20, arcing will typically occur and such arcing currents are almost exclusively in phase with the applied voltage. That is, the shield current will be in phase with the active voltage. Phase sensing circuitry 104 detects this in phase, fault condition to change the output from high to low.

Spectral sensing or filtered bandwidth circuitry 106 provides a further reliable means for detecting the presence of arcing between the active electrode and shield. Moreover, this method does not need access to the active electrode voltage and thus readily lends itself to those monitor circuits 32 which are located outside the host electrosurgical generator 36. As will be described in more detail hereinafter with respect to FIG. 10, spectral sensing circuitry is responsive to at least one predetermined bandwidth of the sensed shield current to detect the presence of a shield current produced by arcing where the arcing will typically occur between the active electrode and the shield due to insulation breakdown therebetween.

Both the phase sensing circuitry 104 and the spectral sensing circuitry 106 also apply inputs to processing and decision circuitry 89 in a manner similar to that described above with respect to circuits 86 and 88 whereby the outputs of circuits 104 and 106 may be utilized to actuate indicators 94 and data logger 102 and deactivate the electrosurgical generator via relay 100.

As indicated above, one or more of the sensing circuits 86, 88, 104, and 106 may be independently utilized or utilized in combination to effect the shield monitor function of circuitry 32.

Various measures have been taken in the present invention to render the operation thereof fail-safe. For example, if the monitor circuitry 32 is employed outside host electrical generator 36, there is a possibility the user may connect the return electrode directly into the electrosurgical generator rather than through the monitor circuitry 32 as illustrated in FIG. 2. If this occurs, the shield will not be connected to the return electrode lead through a low impedance path, as will be discussed below, and thus monitor circuitry 32 will be inhibited from performing its monitoring function. To provide an alert to the user that the return electrode has been inappropriately directly connected to the generator 36, a shield to ground voltage sensor 87 may be provided, the sensor 87 being responsive to the shield voltage over line 85 via cable 34. The output of shield/ground voltage sensor 87 is applied to processing and decision circuitry 89 where an appropriate indicator 94 is actuated if the return electrode is directly connected to the electrosurgical generator.

If the return electrode is directly connected to the electrosurgical generator, the voltage on the shield will rise to a substantial percentage of the active voltage in view of an open circuit between the shield and the return electrode lead. Hence, whenever the voltage on the shield exceeds a predetermined threshold as will be discussed in more detail with respect to FIG. 12, an appropriate signal is applied to processing and decision circuitry 88 over line 91 to thereby provide a desired alert.

Furthermore, when the monitor circuitry 32 is provided outside host electrical generator 36, it is desirable in some instances to battery power the monitor circuitry 32. That is, if the monitor circuitry is powered from an operating room electrical outlet, this will entail an additional wire being connected to the monitor circuitry where in some instances it is desirable that the number of wires associated with the electrosurgical apparatus be reduced to a minimum. Accordingly, an activation control unit 93 may be employed which is responsive to the sensed shield current over line 95 or the sensed return current over line 97 to provide a battery power supply for the various circuits of monitor circuitry 32 as will be described in more detail hereinafter with respect to FIG. 13.

Figure 10:
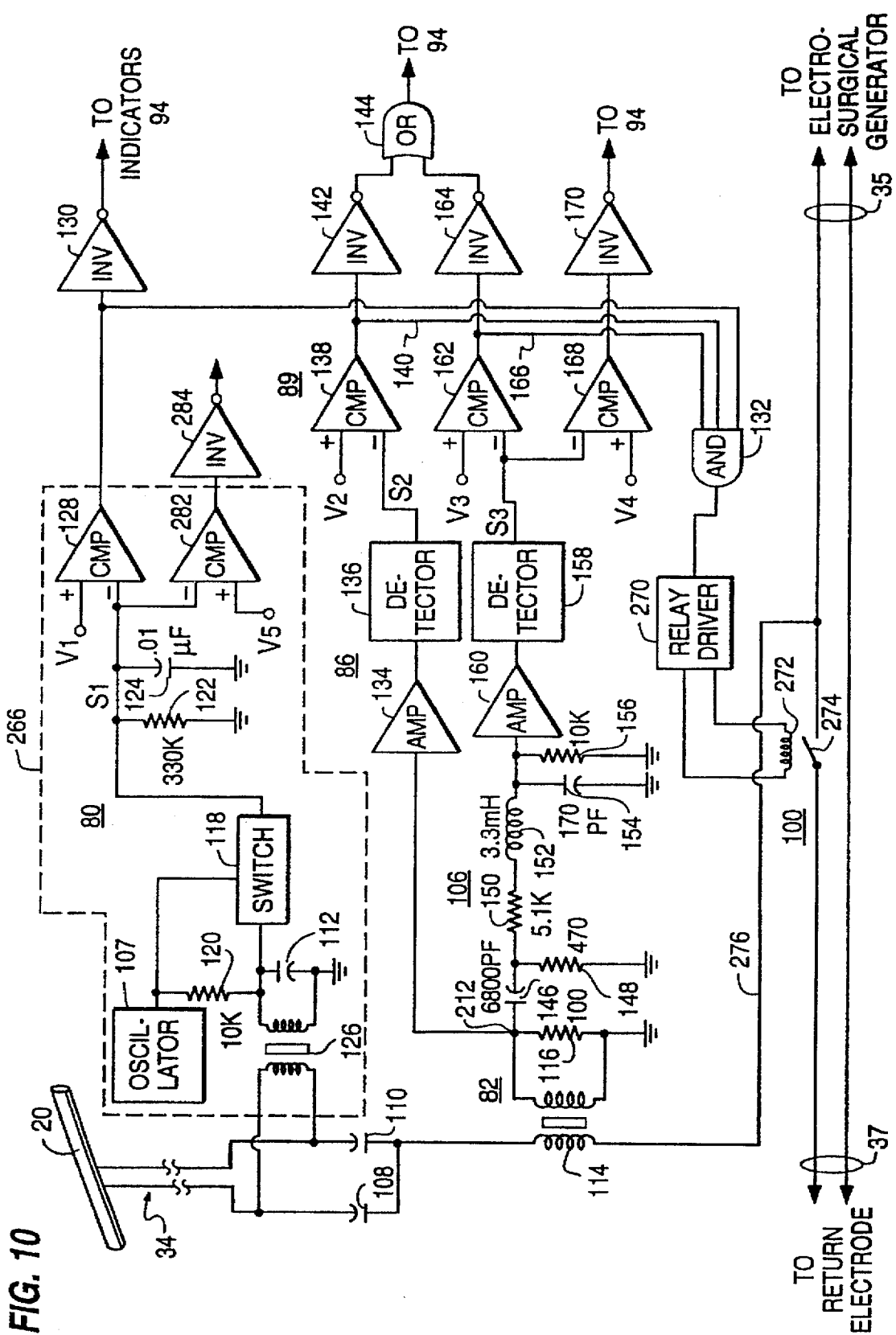
FIG. 10 is a schematic diagram of the monitor circuitry of FIG. 9 where full bandwidth amplitude and spectral sensing (or filtered bandwidth) measurement circuitry are illustrated in further detail.

In FIG. 10, the full bandwidth amplitude sensor 86 and the spectral sensing circuitry 106 of FIG. 9 are illustrated in further detail together with the conductivity monitor 80 for monitoring the integrity of the connection of shield connector 34. The conductivity monitor 80 comprises a square wave oscillator 107 which is tuned to resonance with a network of capacitors 108, 110 and 112. The path from shield 20 to the return electrode lead comprises cable 34, capacitors 108 and 110, transformer 114, and resistor 116. This path has a low impedance-typically less than 20 ohms, to thus provide a low impedance pathway for any current coupled to shield 20.

A switch 118 is driven in phase with the voltage across capacitor 112 as it responds to oscillator 106. A resistor 120 connects the oscillator to capacitor 112. Resistor 122 and capacitor 124 provide a voltage $S_1$, the amplitude of which is inversely proportional to the amplitude of the monitor current provided by oscillator 107 through the redundant cable 34.

In operation, the oscillator applies a signal of approximately 15 KHz to capacitor 112 via resistor 120. This signal is coupled by transformer 126 across dual redundant cable 34. As long as the cable 34 is properly connected to shield 20 a path will be provided for the oscillator signal which will be reflected back through transformer 126. Since switch 118 is operated at the frequency of oscillator 107, the signal reflected back through transformer 126 will be synchronously detected at 118 and applied to the demodulator comprising resistor 122 and capacitor 124 where switch 118 may a 4066 transmission gate or an FET. The electrosurgical frequency (typically 750 KHz although other electrosurgical frequencies may be employed) will be rejected by the synchronous detector and thus conductivity monitor 80 is sensitive only to the conductivity monitoring signal generated by oscillator 107.

As long as the cable 34 is properly connected to shield 20, the signal amplitude developed at capacitor 124 will be less than the reference voltage $V_1$ established applied to comparator 128. Accordingly, the output of comparator 128 will be high during this time and the output of inverter 130 will be low and thus no alert will be provided by indicators 94 of FIG. 9. The function of comparator 282 and inverter 284 will be described hereinafter.

If the cable 34 is not properly connected to shield 20, the voltage developed across capacitor 124 will exceed the reference voltage $V_1$ and thus the output of comparator 128 will go low and the output of inverter 130 will go high to thereby generate a fault alert "connection" at indicators 94 of FIG. 9.

The output of comparator 128 is also applied to an AND circuit 132 which in turn is connected to relay 100. As long as all the inputs to AND circuit 132 are high, a signal will be applied to relay coil 272 via relay driver 270 to thus close the contact 274 of relay 100 and establish the connection between the return electrode and the return terminal of the generator. If the output of comparator 128 goes low because of a faulty connection of cable 34 to shield 20, the output of AND circuit 132 will go low to thus de-energize relay 100 and thus prevent activation of the generator until the cable is properly connected to the shield.

The shield current sensor 82 of FIG. 9 comprises transformer 114 and resistor 116. The full bandwidth amplitude sensor 86 comprises an amplifier 134 and a detector 136. Thus, the unfiltered shield current sensed at 82 is converted to a proportional voltage by detector 136 where the output of detector 136 is applied to a comparator 138. As long as $S_2$, the output of detector 136 does not exceed reference voltage $V_2$, the output of comparator 138 remains high to thus enable AND circuit 132 over line 140. If the value of the sensed shield current exceeds the threshold established by $V_2$, the output of comparator 138 will go low to thus disable AND circuit 132 and thus de-energize relay 100 thereby deactivating the electrosurgical generator. Moreover, if the output of comparator 138 goes low the output of inverter 142 will go high as will the output of OR circuit 144 to thus generate a fault alert "shield current" at indicators 94 of FIG. 9.

Spectral sensing or filtered bandwidth circuitry 106 comprises a band pass filter, the band pass at the 3 db points of which are about 50 KHz to 250 KHz. The filter comprises a capacitor 146, a resistor 148, a resistor 150, an inductor 152, a capacitor 154, and a resistor 156. The filter may be of the Butterworth or any other suitable type to effect the desired band pass function.

The output of the filter is applied to a detector 158 through a amplifier 160 where detector 158 generates a signal proportional to the signal energy passed by the filter. Detectors 136 and 158 may be RMS to DC convertors such as the LT 1088 made by Linear Technology, Inc.

As indicated above, a typical electrosurgical operating frequency is about 750 KHz while other operating frequencies such as 500 to 750 KHz may also be employed in accordance with the invention although there is no intent to be limited to a particular operating frequency. The bandpass of 50 to 250 KHz is particularly indicative of whether an arcing current is present although other bandpasses may be used as long as they are appropriately indicative of whether an arcing current is present.

If the output of detector 158 exceeds a first threshold voltage $V_3$ applied to a comparator 162, the output of the comparator will be switched from its normal high condition to a low condition such that a high signal will be provided at the output of OR circuit 144 through inverter 164 to thereby provide a fault alert "shield current" to indicators 44 of FIG. 2. Moreover, AND circuit 132 will be disabled over line 166 to thus deenergize relay 100 and deactivate the electrosurgical generator.

The output of detector 158 is also applied to a comparator 168, the threshold voltage $V_4$ of which is less than $V_3$. Thus, if the output $S_3$ of detector 158 exceeds $V_4$ but does not exceed $V_3$, this is an indication that the insulation between active electrode 14 and shield 20 is beginning to break down but has not completely broken down (where complete breakdown corresponds to reference $V_3$). Accordingly, in this situation where $S_3$ exceeds $V_4$ but not $V_3$, the output of comparator 168 will be switched from its normal high condition to a low output. The low output is inverted at inverter 170 to thus provide a warning alert at indicators 94 of FIG. 9.

The full bandwidth amplitude sensor 86 need not necessarily be employed inasmuch as the bandpass filter of spectral sensing circuitry 106 does have some response at the operating frequency where the operating frequency for the filter of FIG. 10 would typically be about 500 to 750 KHz. Therefore, the filter is sensitive to the high currents flowing during an insulation breakdown. Accordingly, the spectral sensing circuitry 106 of FIG. 10 can also perform the full bandwidth amplitude sensing function of circuitry 86. In this regard, it should be noted, insulation breakdowns tend to produce high shield currents. Moreover, normal shield current is also rather large where the normal shield current is capacitively coupled to the shield from the active electrode, as discussed above with respect to phase sensing circuitry 104. Hence, the normal and fault currents can be rather close to one another in absolute amplitude. The range of currents in one embodiment under normal conditions has been measured to be about 50 to 250 ma RMS depending upon the quality of insulation used, the type of waveform applied, and the control setting of the generator. Fault condition currents in this embodiment may be in the range of 300 to 1500 ma RMS. The closeness of these limits leads to difficulty in some situations in distinguishing between normal and fault conditions if the determination is based on absolute RMS current alone as detected by sensor 86. However, testing has demonstrated that with a band pass filter such as the filter of spectral sensing circuitry 106, the differentiation is substantially improved. For a "coagulation" waveform, where breakdown is most likely, there is typically a 4:1 differentiation between the top of the normal range and the bottom of the abnormal range. Accordingly, the spectral sensing circuitry 106 is very reliable in detecting an arcing current indicative of insulation breakdown.

With respect to the processing and decision circuitry 89 of FIG. 9, it should be noted that the comparators 128, 138, 162 and 168, the inverters 130, 142, 164 and 170, AND circuit 132, and OR circuit 144 comprise the elements of FIG. 10 which correspond to circuitry 89, there being no intent to limit the invention to this particular decision circuitry.

Illustrative values are given for certain components of FIG. 10 and other figures of the drawing where resistance is in ohms. There is no intent to limit the invention to these values.

Figure 11:
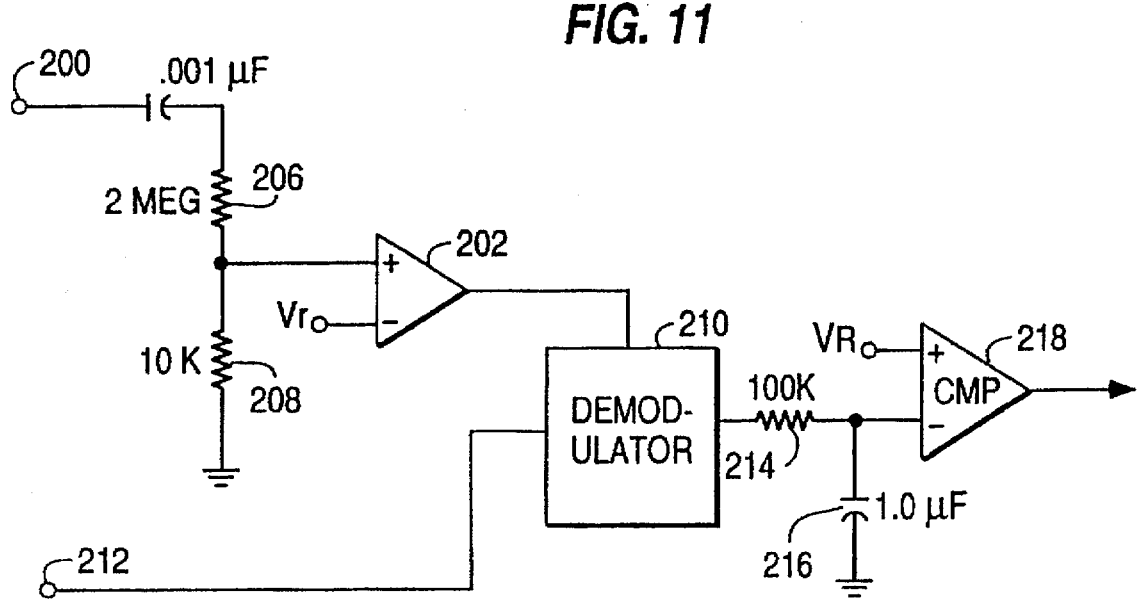
FIG. 11 is a schematic diagram of illustrative phase sensing circuitry for use in the invention.

Referring to FIG. 11, there is illustrated in further detail the phase sensing circuitry 104 of FIG. 9. The active electrode voltage is applied to terminal 200 and coupled to the positive terminal of a comparator 202 via a capacitor 204 and a voltage divider comprising resistors 206 and 208. The reference voltage $V_r$ applied to the negative terminal of comparator 202 is such as to provide a substantially square wave signal at the output of comparator 202, the frequency and phase of which corresponds to that of the active voltage applied to terminal 200 where this square wave signal is applied to an input of a demodulator 210 which may be an analog transmission gate such as a Motorola MC 1596.

Applied to the second input of the demodulator is the sensed shield current which corresponds to the voltage across resistor 116 of FIG. 10 at terminal 212. The output of the demodulator is applied to an RC circuit comprising resistor 214 and capacitor 216 where the output of the RC network is applied to the negative input of a comparator 218. Applied to the positive input of the comparator is reference voltage $V_R$, which may be adjusted to correspond to approximately 100 ma of shield current in phase with the active voltage. Thus, in an arcing situation (corresponding to damaged installation or the like), the shield current will be in phase with the active voltage, as discussed above, whereby the voltage across capacitor 216 will exceed the reference voltage $V_R$ to thus switch the output of converter 218 from high to low.

Assuming the phase sensing circuitry 104 is employed rather than the spectral sensing circuitry 106, the switching of the output of comparator 218 from high to low would deactuate AND circuit 132 to open relay 100 whereby the generator would be deactivated and an alert condition would be applied from the output of OR circuit 144 to appropriate indicators 94.

Figure 12:
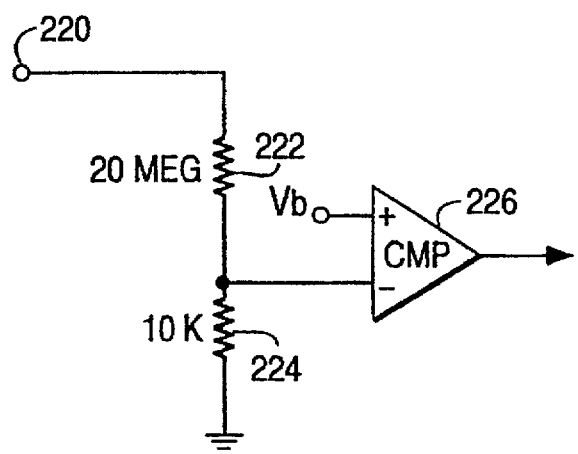
FIG. 12 is a schematic diagram of illustrative shield-to-ground voltage sensing circuitry in accordance with the invention.

Referring to FIG. 12, the shield/ground voltage sensor 87 is illustrated in further detail where the voltage at terminal 220 is the voltage on shield 20, as indicated in FIG. 9. This voltage is applied through a voltage divider comprising resistors 222 and 224 to the negative input of a comparator 226. The resistor 222 is preferably rated to withstand the high voltage which may occur on the shield if the monitor circuitry 32 is not connected to the return electrode whereby, as discussed above with respect to FIG. 9, the voltage on the shield will approach the full active voltage. Connected to the positive input of comparator 226 is a reference voltage $V_b$ where $V_b$ in a typical application corresponds to 100 to 300 volts on shield 20. That is, the voltage $V_b$ may be approximately 0.5 to 1.5 volts.

In operation, whenever the voltage applied to the negative input of comparator 226 exceeds the reference voltage $V_b$, the output of the comparator will change from its normal high level to a low level whereby a fault alert may be generated at the output of OR circuit 144 as described above and a generator deactivate signal may be generated at the output of AND circuit 132 as also described above with respect to the phase sensing circuitry.

Figure 13:
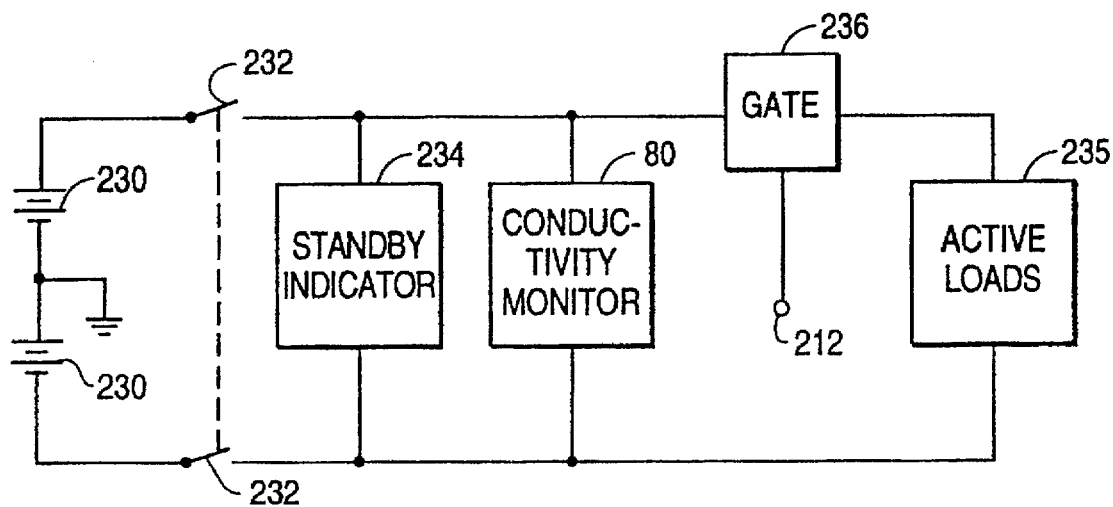
FIG. 13 is a schematic diagram of illustrative battery activation control circuitry in accordance with the invention.

Referring to FIG. 13, there is illustrated battery activation control unit 93 of FIG. 9 which includes batteries 230, ganged switches 232, standby indicator 234, and gate 236. In operation, switches 232 are closed in response to shield cord 34 being connected to shield monitor circuitry 32. Although means are not specifically shown, such means are known whereby upon insertion of a plug into a circuit, a switch may be mechanically closed to effect a further function and such means would be employed to close ganged switches 232 in response to the shield cord being connected to monitor circuitry 32.

Upon closure of switches 232, standby indicator 234 is actuated to indicate a standby status of the monitor circuitry 32. Moreover, the voltage from batteries 230 is applied to conductivity monitor circuitry 80 of FIG. 9 whereby the conductivity monitor may provide an indication to the user that cable 34 has been properly connected to shield 20. If not, an alert is provided to the user as described above with respect to conductivity monitor 80.

Moreover, the voltage from batteries 230 is applied to gate 236 as a power supply voltage therefore whereby the gate 236 is primed to apply the voltages from batteries 230 as power supply voltages to the remaining circuits of the monitor 32 of FIG. 9 which are illustrated as active loads 235 in FIG. 13. That is, gate 236 is responsive to the sensed shield current established at terminal 212 of FIG. 10. As soon as this current is sensed, all of the circuits of the monitor are powered by batteries 230.

Another consideration relating to fail-safe operation is that, when the shield monitor circuitry 32 is utilized outside the host electrosurgical generator, the shield must not become the return electrode. Accordingly, an adaptor, as schematically illustrated in FIG. 14, may be utilized to insure that the return electrode is properly connected to the monitor circuitry 32.

Figure 14:
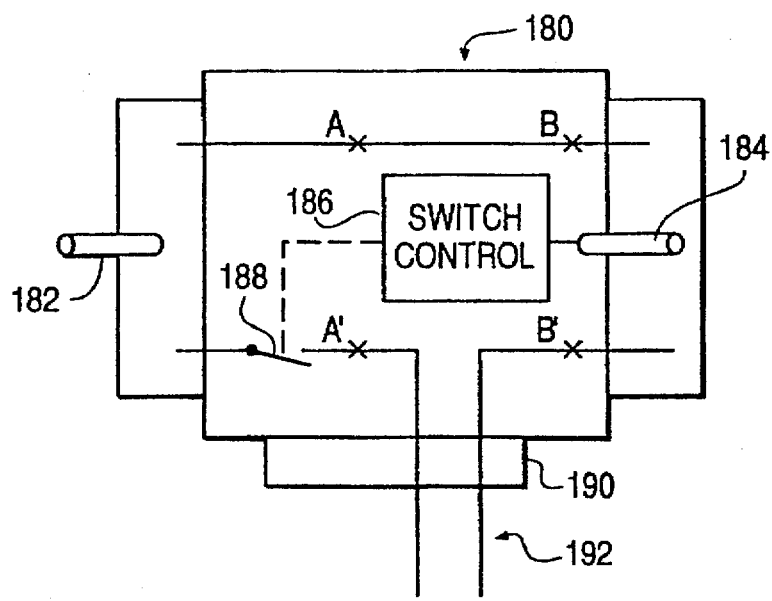
FIG. 14 is a schematic diagram of an illustrative adaptor for use with the shield monitor circuitry of this invention.

In particular, referring to FIG. 14, the adaptor is indicated at 180 and includes a pin 182 which connects to the return terminal of the electrosurgical generator in a conventional manner to indicate to the generator the use of a dual-area return electrode. That is, pin 182 corresponds to a pin employed in an industry standard connector whereby the generator will not operate until the return electrode is properly connected to the return terminal of the generator.

Receptacle 184 of adaptor 180 is adapted to receive the abovementioned standard pin of the return electrode plug. In a manner similar to that conventionally employed in the generator, the adaptor 180 includes a switch control mechanism 186 which is responsive to the insertion of the return electrode plug pin into receptacle 184 to close a switch 188 in the adaptor and thus close the connection of the return electrode to the electrosurgical generator through the adaptor.

The adaptor 180 additionally includes a port 190 by which the adaptor can be connected to monitor circuitry 32 via a two wire cord 192. When the cord is connected to the monitor circuitry 32, the points A, A' and B, B' shown in FIG. 14 respectively correspond to the same points shown in FIG. 9 where return current sensor 96 and relay 100 are incorporated in monitor circuitry 32 and switch 188 is incorporated in adaptor 180 and where cord 192 is not shown in FIG. 9.

Thus, unless the return electrode 40 is connected to adaptor 180 via receptacle 184, switch 188 will not be closed and hence the generator can not be activated even though pin 182 of the adaptor is properly connected to the generator. Accordingly, the shield cannot become the return electrode. Moreover, if use is attempted without the return electrode plug pin being inserted into receptacle 184, a fault condition may be presented at indicators 94. That is, a signal may be generated by means (not shown) over line 99 of FIG. 9 and applied to circuitry 89 where the signal is generated depending on the position of switch 188.

Figure 15:
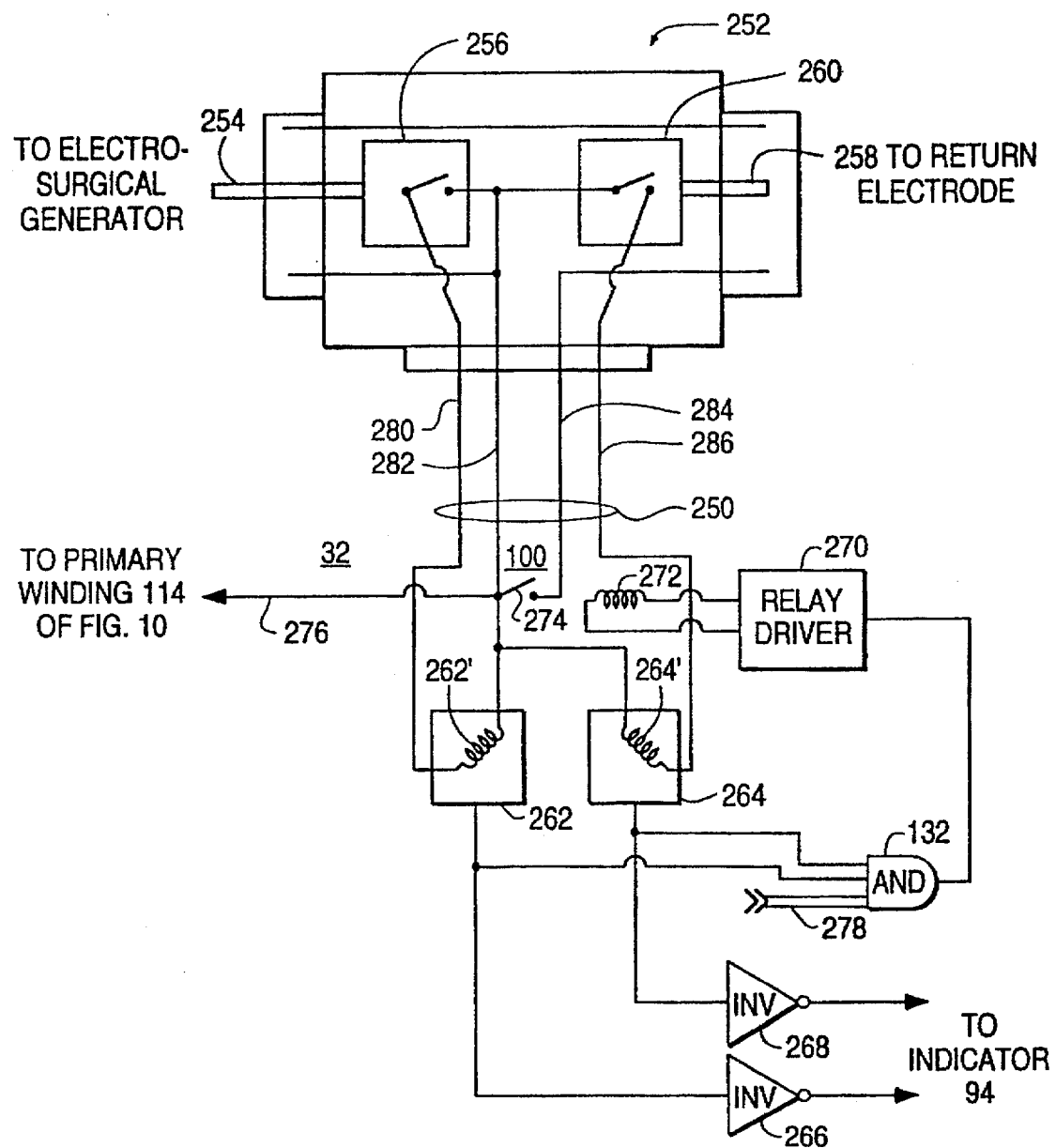
FIG. 15 is a schematic diagram of another illustrative adaptor together will further illustrative shield monitor circuitry for use in this invention.

In the embodiment of FIG. 15, a four wire connection or cord 250 is utilized between an adaptor 252 and monitor circuitry 32 where the monitor circuitry is partially indicated at 32 in FIG. 15 as will be described in more detail below. Adaptor 252 includes a pin 254 which corresponds to pin 182 of adaptor 180 of FIG. 14. Moreover, pin 254 is associated with a switch 256 whereby the switch 256 is closed in response to adaptor 252 being attached to the return terminal of the electrosurgical generator. Adaptor 252 also includes a receptacle 258 which corresponds to receptacle 184 of adaptor 180. Thus, adaptor 252 includes a switch control mechanism (not shown), which is responsive to the insertion of the return electrode plug pin to close a switch 260 in the adaptor.

The adaptor 252 further differs from adaptor 180 in that in adaptor 180, switch 188 is in series with one of the generator return leads whereas in adaptor 252 the switches 256 and 258 are referenced to this lead.

In order to detect proper connection of adaptor 252 to the generator via switch 256 and proper connection of the return electrode to the adaptor via switch 260, continuity monitors 262 and 264 are provided where each of these monitors corresponds to the continuity monitor circuitry indicated at 266 in FIG. 10 within the dotted lines. The output of each continuity monitor is applied to AND gate 132, which is shown in both FIGS. 10 and 15. The output of AND circuit 132 is applied to relay driver 270 which drives the coil 272 to, in turn, actuate the contact 274 of relay 100. The outputs of the continuity monitors are also applied to inverters 266 and 268 respectively. The outputs of inverters 266 and 268 are applied to appropriate indicators 94.

When the adaptor 252 of FIG. 15 is employed, the shield return lead 276 is connected to the generator return lead as shown in FIGS. 9, 10, and 15. Thus, when the adaptor 252 is employed, four separate transformers are incorporated in monitor circuitry 32 where two of these transformers correspond to transformers 114 and 126 of FIG. 10 and the other two transformers are associated with conductivity monitors 262 and 264, the primaries of these transformers being indicated at 262' and 264'. In particular, the primary windings 262' and 264' each serve the same function as the primary of transformer 126; thus, when the monitor circuitry 32 is employed with adaptor 252 of FIG. 15, the monitor circuitry will incorporate three separate conductivity monitors—that is, conductivity monitor 80 (shown in FIG. 10) and the conductivity monitors 262 and 264 of FIG. 15.

In operation, the adaptor 252 provides fail-safe operation in that if the adaptor is not properly connected to the generator, AND circuit 132 will be disabled to thus present this fault condition at indicators 94. In particular, if switch 256 is open, thereby indicating lack of attachment of the adaptor to the return terminal of the generator, an open circuit condition will exist across the primary 262' to thus provide a low output signal from conductivity monitor 262, as described hereinbefore with respect to conductivity monitor 80 of FIG. 10. This in turn will present this fault condition at indicators 94.

In a similar manner, if the return electrode is not connected to the adaptor, switch 260 will be open to thus provide an open circuit condition across the primary winding 264'. Accordingly, the output of conductivity monitor 264 will go low to disable AND circuit 132 and open relay 100 and to present this fault condition at indicators 94. The additional inputs to AND circuit 132 shown in FIG. 10 are indicated at 278 in FIG. 15.

It should be noted that the particular situation that switch 256 protects against is that where a first return electrode lead is inadvertently directly connected to the generator and a second return electrode lead is connected to receptacle 258 of adaptor 252. However, contact 274 of relay 100 of adaptor 252 is not connected to the return electrode circuit of the generator and thus monitor 32 can not disable the generator. However, switch 256 will warn against the foregoing situation by providing an appropriate alert at indicator 94.

If it is considered not necessary to protect against this situation, switch 256 need not be incorporated in adaptor 252. In this case, switch 256 and wire 280 would be eliminated together with conductivity monitor 262. Thus, the resulting connection between adaptor 252 and monitor circuitry 32 would be a three wire cord comprising wires 282, 284 and 286 where switch 260 is referenced to one of the generator return leads.

As described above, and as will be further described hereinafter, various circuits may be employed to provide fail-safe operation of shield monitor circuitry 32. Thus, as stated above, the circuitry of FIG. 15 utilizes four transformers to monitor various conditions. Moreover, the number of transformers may be reduced while still monitoring the same number of conditions by having each condition correspond to a particular frequency and thus detecting each condition by appropriate frequency discrimination circuitry. Other techniques will also occur to those of ordinary skill in this art.

As discussed above, one of the conditions which may be protected against to provide fail-safe operation includes the shield 20 not being connected to the shield monitor where shield continuity monitor 80 of FIG. 10 provides this fail-safe function. Moreover, by employing an additional comparator 282 (FIG. 10), it is possible to monitor not only a lack of connection of the shield to monitor circuitry 32 but also a poor connection. Reference voltage $V_5$ is applied to comparator 282 and is less in magnitude than the reference $V_1$ applied to comparator 128. Thus, comparator 282 detects a poor connection if the voltage across capacitor 124 exceeds $V_5$ but is less than $V_1$ whereby the output of comparator 282 goes low and is inverted by inverter 284 to provide an indication of the poor connection.

When the adaptor 252 of FIG. 15 is not plugged into the return terminal of the generator but rather the return electrode is improperly directly attached to the return terminal, this will be detected inasmuch as switch 260 of FIG. 15 will not be closed whereby indicators 94 will provide an appropriate alert.

Figure 16:
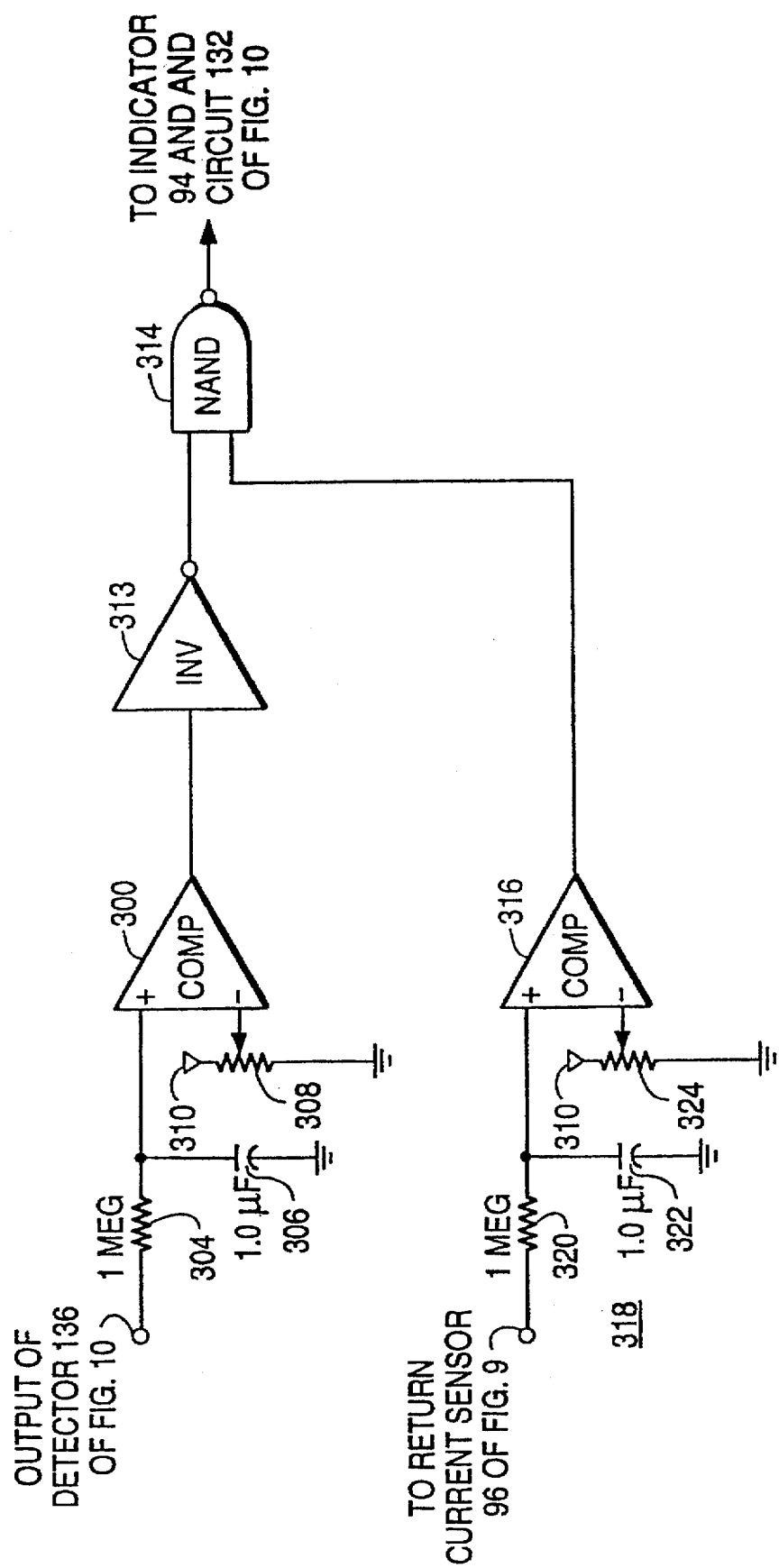
FIG. 16 is a schematic diagram of illustrative circuitry for protecting against failure to insert an accessory into a shield properly connected to the monitor circuitry.
Figure 17:
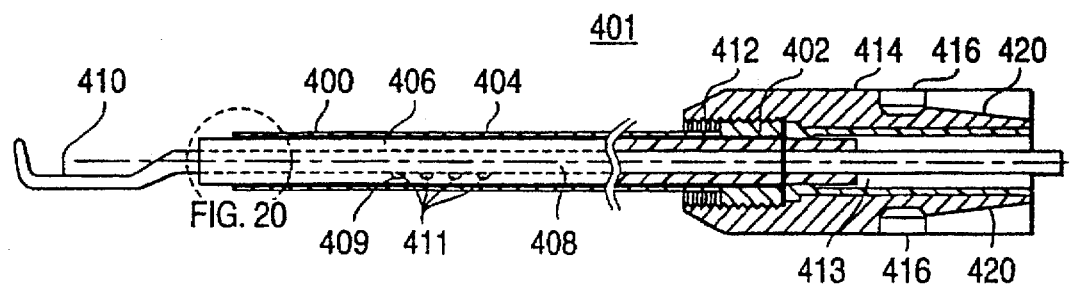
FIG. 17 is a side view in partial cross-section of an illustrative integrated active electrode/shield electrosurgical instrument in accordance with a further aspect of the invention.

Referring to FIG. 16, there is illustrated further protection circuitry in accordance with the invention to protect against the possibility of a user properly connecting the shield to monitor circuitry 32 and the monitor circuitry to generator 36 but not inserting the accessory (or active electrode 14) properly into the connected shield. The accessory would instead be inserted directly into trocar sheath or cannula 10 without a shield or it might be used with a different shield, not the one connected to the monitor. In accordance with the embodiment of FIG. 16, the foregoing possibility is protected against by requiting at least a predetermined minimum mount of shield current to be present when the generator is activated.

If the monitor is disposed within the electrosurgical unit whereby the voltage on the active lead (that is, the voltage between the active and return leads) is readily accessible, the foregoing protective function can be accomplished by sensing a predetermined minimum mount of shield current in the presence of the active lead voltage. The presence of active lead voltage without the predetermined minimum amount of shield current would be interpreted as a fault condition. If monitor unit 32 is disposed outside the electrosurgical generator, the active voltage is less readily accessible and thus the return current may be utilized if the active lead voltage is not sensed. This latter technique is illustrated in the circuitry of FIG. 16.

In FIG. 16, the sensed shield current is obtained from terminal 212 of FIG. 10 and applied to the positive input of a comparator 300 via a filter 302 comprising resistor 304 and capacitor 306. Applied to the negative input of comparator 300 is a reference voltage obtained from potentiometer 308 connected between reference voltage source 310 and ground. The comparator output is applied via invertor 313 to an input of a NAND circuit 314.

The sensed return current is obtained from return current sensor 96 of FIG. 9 and applied to the positive input of a comparator 316 via a filter 318 comprising resistor 320 and capacitor 322. Applied to the negative input of comparator 316 is a reference voltage via a potentiometer 324 connected between reference voltage source 310 and ground. The output of comparator 316 is applied to a second input of NAND circuit 314. The output of NAND circuit 314 is applied to indicators 94 and AND circuit 132 of FIG. 10 to thus provide an appropriate alert of the foregoing condition together with deactivation of the generator.

The filters 302 and 318 are provided because high value of the shield current may not occur at precisely the same time as high value of the return current. For example, a loaded generator may produce high return current but not high shield current. Thus, by storing the sensed values of the shield and return currents with respective filters 302 and 318, it is possible to utilize the return current rather than the active voltage to sense the foregoing condition where the accessory is not properly inserted into a connected shield. In general, the time constants of filters 302 and 318 should be as long as the typical activation period of an electrosurgical generator—that is, about 2 to 3 seconds. Other than filters 302 and 318, more sophisticated methods of signal processing may also be utilized such as peak detection within a time window.

In operation, a high output from NAND circuit 314 indicates a normal condition where the shield current is present in the presence of the return current. Thus, if sensed return current is applied to the positive input of comparator 316 to exceed the threshold established by potentiometer 324, the output of comparator 316 goes high and is applied to NAND circuit 314. Moreover, if sensed shield current is applied to the positive terminal of comparator 300, such that the threshold established by potentiometer 308 is exceeded, the output of the comparator goes high and the output of inverter 313 goes low whereby the output of NAND circuit stays high. However, if there is no shield current which exceeds the threshold established by potentiometer 308, the output of comparator 300 will remain low while that of inverter 313 will remain high. Hence, in this situation both of the inputs to NAND circuit 314 will be high causing the output of the NAND circuit to go low and thus indicate the above described fault condition.

As described above, the present invention is particularly advantageous in that it provides a shield between the trocar sheath and the active electrode whereby the shield may be utilized to effect essentially fail safe operation in electrosurgical laparoscopic procedures. Moreover, the deployment of the safety shield of the present invention may be extended to other procedures where a trocar is not used. For example, in tonsillectomies, the instrument is hand-held and inserted through the mouth, there being no need for a trocar. In addition to tonsillectomies, other similar procedures are deep pelvic procedures requiting long extensions and orthopedic and thoracic procedures, etc. With such hand-held instruments, the element 10, which corresponds to a trocar sheath in FIG. 2 and the other figures of the drawing, may instead correspond to the handpiece of a hand-held instrument—that is, that portion of a hand-held instrument which is held by the surgeon's hand. All of the advantages described above with respect to laparoscopic and like procedures are also realized with hand-held instruments used in open procedures such as laparotomy where again, the shield is connected through a low impedance path to the return electrode and where shield current monitor circuitry 32 is preferably utilized to achieve effectively fail-safe operation.

Figure 20:
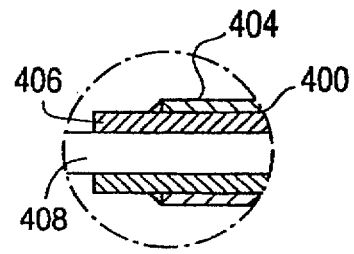
FIG. 20 is an enlargement of an encircled portion shown in dotted lines in FIG. 17.

As described hereinbefore with respect to FIG. 8, the active electrode 18 may be integrally incorporated with the support structure for shield 20 whereby a single, integrated instrument is provided, one advantage of which is set up time is reduced in that only a single instrument need be inserted through trocar cannula 10. Reference should now be made to FIGS. 17–20 which illustrate an integrated active/shield instrument 401 where the shield 400 (which corresponds to shield 20 of FIG. 2) becomes the principal structural element of the accessory. As can best be seen in FIGS. 17, 18, and 20, the shield conductor 400 may be a stainless steel tube. A threaded sleeve 402 is attached to the proximal end of conductor shield 400 by brazing or the like. Outer insulation 404 prevents conduction between shield conductor 400 and the patient's tissues where the outer insulation typically comprises FEP. Plastic tube or extrusion 406 comprises the insulator between active electrode rod 408 and the shield conductor 400. Typically tube 406 may comprise polycarbonate or ULTEM, a registered trademark of General Electric Co. As shown in FIG. 20, the outer insulation 404 and the plastic extrusion 406 extend beyond the metallic shield 400 where the insulation 404 is tightly fitted over the plastic extrusion 406 at the distal end of extrusion 406. The active electrode rod 408 may be provided with various configuration tips, one of which is illustrated at 410 in FIG. 17 where this may comprise stainless steel.

Figure 18:
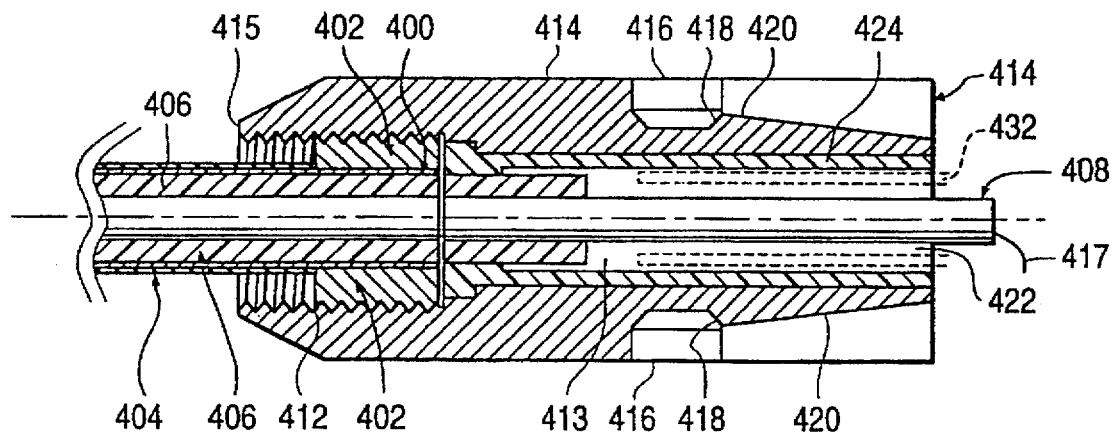
FIG. 18 is an enlargement of the cross-sectional portion of FIG. 17.
Figure 19:
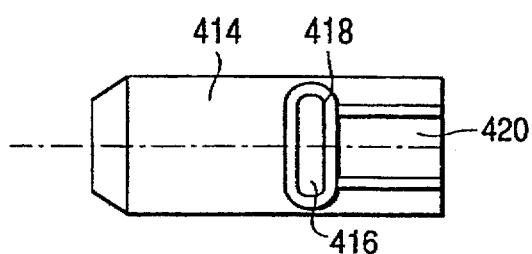
FIG. 19 is a plan view of the instrument body of the electrosurgical instrument of FIG. 17.

Rod 408 may be adhered to extrusion 406 by an appropriate adhesive while extrusion 406 is, in turn, adhered to shield 400 by such adhesive. Alternatively, rod 408 may be slideably disposed with respect to insulative extrusion 406. For example, as illustrated in FIG. 18, rod 408 may be provided with a small projection or ridge 409 which may engage one of a plurality of detents 411 provided in extrusion 406 whereby the position of the rod with respect to the extrusion may be adjusted over a range of 0.7 inch, for example, by manual insertion or withdrawal of the rod with respect to the extrusion so that the ridge 409 engages a desired one of the detents 411. Such an adjustment range allows the exposed electrode tip 410 to be tailored by the surgeon to the specific requirement of the application. Of course, other known mechanical arrangements can be utilized to effect the foregoing adjustment range.

The diameter of shield tube 400 with insulation 404 thereon may be 5 millimeters or less and thus may be inserted through a trocar cannula 10 (see FIG. 2) having an opening as small as 5 millimeters, for example. A threaded sleeve 402 attached to the distal end of shield tube 400 is threaded into a threaded portion 412 of a passageway 413 which extends through the instrument body 414. The instrument body typically comprises stainless steel and the distal end 415 thereof may butt against the proximal end of trocar cannula 10 after insertion of the shield 400 of the integrated active-shield instrument 401 through the cannula. The instrument body 410 is maintained at the potential of the shield and thus close to the patient potential as described hereinbefore (that is, the impedance between (a) the instrument body 414 and the shield 400 and (b) the return lead of the electrosurgical generator should be less than about 20 ohms and/or the voltage on the instrument body and the shield should be less than about thirty volts) whereby the instrument body may be safety touched by a surgeon without concern for electrical shock or burn.

In accordance with a further aspect of the invention, the body 414 is adapted to receive a unique connector assembly which will be described in more detail hereinafter. For example, the cross-sectional configuration of the body 414 may be substantially square where on opposite sides of the body 414 are provided indentations 416 where one of the indentations is shown in plan view in FIG. 19. The purpose of the indentations 416 is to provide receptacles (or electrical terminals) for the dual shield monitor connectors corresponding to the conductors 34 of FIG. 2 where one of the conductors 34 is connected to one of the indentations 416 and the other conductor is connected to the other indentation 416. Since the instrument body 414 is maintained at shield potential in accordance with this present embodiment of the invention, it can be seen that connection of the dual shield monitor circuitry conductors 34 to shield body 414 facilitates such connection. The indentations are bevelled at the lower portions 418 and the instrument body is provided with a pair of inclined grooves 420 which communicate with the indentations 416 to further facilitate connection of the shield monitor conductors to the instrument body, as will be described in more detail below.

Connector rod 408 extends through instrument body 414 such that an annular opening 422 is provided at the proximal end of the passageway 413. This annular opening receives an insulated tube 432 from the connector assembly as will be described in more detail hereinafter. Furthermore, the passageway 413 is provided with an insulating sleeve 424 secured to the proximal end thereof and typically comprising polycarbonate or ULTEM.

Referring now to FIGS. 21–24, there is illustrated an integrated connector assembly 428 in accordance with the present invention which contains both the electrosurgical active and the shield conductors in a single connector. The integrated connector assembly comprises an insulating core member 430 which includes a tubular tip portion 432 extending therefrom. A bore 434 extends through tip portion 432 and the main body of the core member 430. Disposed within the bore is a female receptacle 436 which receives the proximal end 417 of the active electrode rod 408 of the integrated active/shield instrument of FIGS. 17–20. The receptacle 436 is connected to the active line 438 (line 38 of FIG. 2) from the electrosurgical generator. The length of receptacle 436 is such that rod 408 can be adjusted over the above-discussed length of 0.7 inch, for example, while maintaining contact between rod 408 and receptacle 436 to thus maintain application of active potential to active electrode rod 408.

Figure 22:
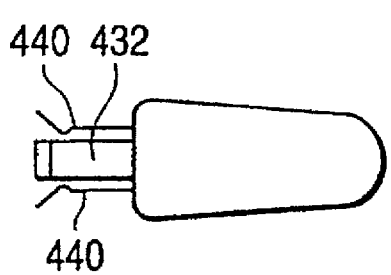
FIG. 22 is a plan view of the integrated connector assembly.
Figure 23:
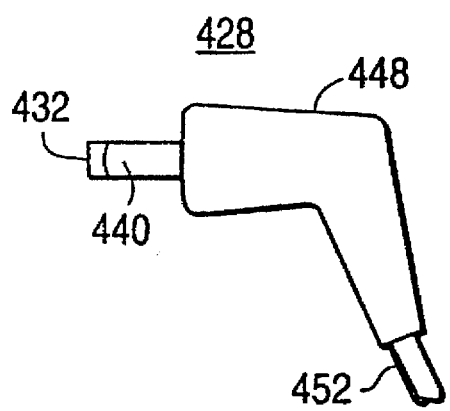
FIG. 23 is a side view of the integrated connector assembly.

Spring contacts 440 are attached to opposite sides of core member 430 by ultrasonic staking or the like at 442. The proximal ends 444 of contacts 442 are connected to a pair of shield monitor conductors 446 by spot welding or the like. A plastic molding 448 is then provided around the foregoing structure where the shape of molding 448 may be as illustrated in FIGS. 22 and 23 whereby the instrument body 414 and connector assembly 428 may comprise a pistol-type instrument after the connector assembly is attached to the instrument body. Other shapes may, of course, also be provided.

Figure 24:
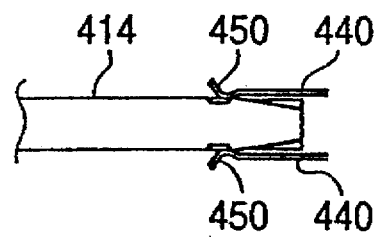
FIG. 24 diagrammatically illustrates attachment of the integrated connector assembly of FIG. 22 to the integrated active/shield electrosurgical instrument of FIG. 17.

Attachment of the integrated connector assembly 428 to the body 414 is facilitated by arcuate distal ends 450 of the spring contacts 440. As can be seen in FIG. 24, attachment of the connector 428 to body 414 causes the distal ends 450 to ride up the inclines 420 and then engage the bevelled bottoms in indentations 416. This feature is particularly advantageous in that a significant insertion and withdrawal force between the integrated connector and the integrated active/shield instrument can be obtained and controlled. Typically this force is relatively significant, for example 3 to 4 pounds, and is stable over a large number of insertions. This is in contradistinction to present electrosurgical active plugs which are not well controlled with respect to the insertion force.

Upon attachment of the active/shield instrument to the integrated connector 428, the insulating tip 432 will extend into the annular opening 422 of instrument body 414 as indicated by the dotted lines in FIG. 18 where the insulating tip 432 snugly fits within the insulator robe 424 of instrument body 414. Accordingly, the insulating robes 424 and 432 cooperate to provide lengthy overlapping insulation so that there is a long path presented to surface electrical breakdown and thus the risk of insulation failure is minimized. This feature is in contradistinction to current standard practice where the active is connected with a standard banana plug. This allows for the possibility of a spark through the surgeon's glove particularly if a drop of water is present at the juncture between the instrument stub and the connector. Because of the long surface breakdown length provided by the combined lengths of the tubes 424 and 432, the probability of such sparking in the present connector is substantially eliminated.

It should also be noted with respect to the spring contacts 440 that they make electrical contact with the shield conductor 400 via instrument body 414 in two separate places thereby providing the dual connection necessary for the monitoring current from shield monitor circuitry 32 over lines 34, as shown in FIG. 2.

Figure 21:
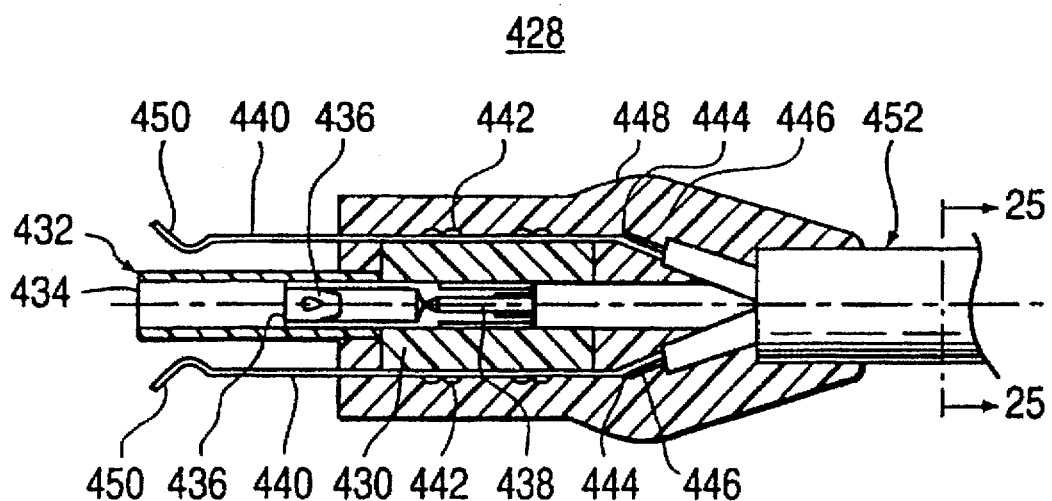
FIG. 21 is a cross-sectional view of an integrated connector assembly in accordance the present invention.
Figure 26:
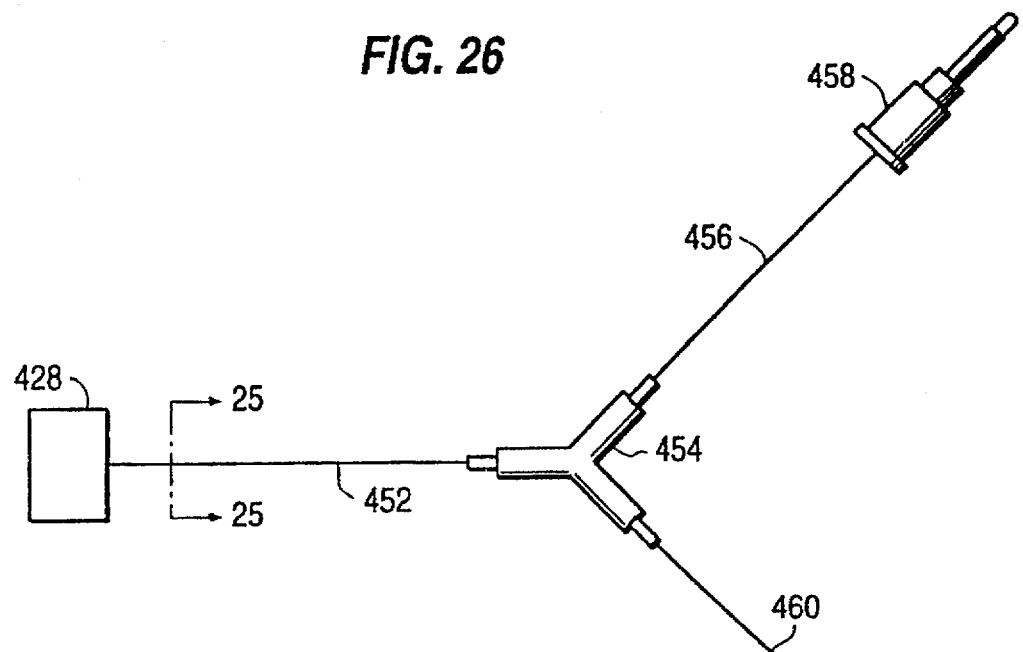
FIG. 26 is a diagrammatic illustration of the integrated cable of FIG. 25 in assembly with separate active and shield connectors.
Figure 25:
FIG. 25 is a cross-sectional view of an integrated active conductor/shield conductor cable, in accordance with a further aspect of the invention taken along the line 25—25 of FIG. 21.

Referring now to FIGS. 21, 25 and 26, there is illustrated a unique low capacitance cable 452 in accordance with the present invention whereby the active conductor 438 and the shield monitor conductors 446 are incorporated into cable 452 as can be seen in FIG. 25. High voltage insulation is provided between the active and shield conductors (typically 7,000 volts peak). Moreover, the oval shaped configuration of conductor 452 is suitable for not only providing flexibility to cable 452 but also minimizing coupling capacitance between active conductor 438 and shield conductors 446. In particular, the capacitance is maintained below a level which would be detrimental to the quality of the electrosurgical waveforms.

The length of cable 452 is typically about two feet and thus the shield and active conductors are run in one cable over a distance which will minimize clutter in the operative field. Of course, the length of the cable can vary to insure minimization of such clutter. Separation of the active and shield conductors after about two or three feet at separator block 454 will further tend to minimize capacitance between active lead 456 and shield leads 460 of FIG. 26 where the active lead 456 is connected to a plug 458 suitable for connection to the electrosurgical generator 36 while the shield leads 460 are connected to a plug 462 suitable for connection to shield monitor circuitry 32.

Figure 27:
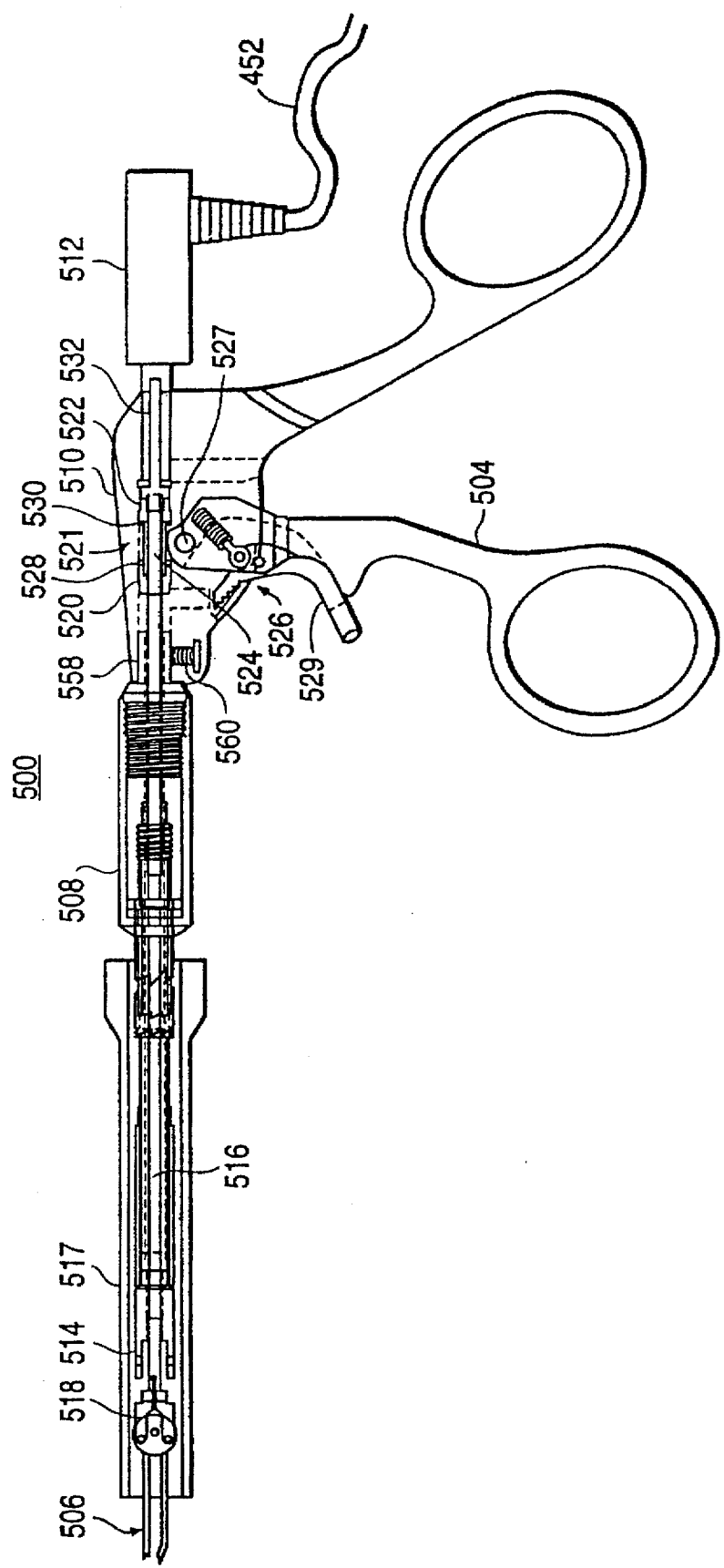
FIG. 27, is a partial schematic, partial cross-sectional view of a articulable instrument in accordance with the invention.

Reference should now be made to FIG. 27 which illustrates an articulable instrument 500 in accordance with the present invention wherein tips 506 such as jaws or the like may be articulated in response to motion of a trigger 504. The articulable instrument 500 generally includes a front end assembly 508, a handle 510 and a unitary connector 512 which connector may exactly correspond to the unitary connector 428 of FIG. 21 where the shape thereof may be as illustrated in FIG. 27 as opposed to the shape illustrated in FIG. 23.

In general, the tips 506 may be of various conventional types and usually have the purpose of grasping or cutting tissues. The tips per se do not form a part of the present invention. Moreover, the yoke 514, which includes a pin for connecting the tips to the yoke (where the tips or jaws are shown at right angles to the yoke in FIG. 27), may also be conventional and as such does not per se form a part of the present invention.

In accordance with a primary aspect of the invention, the front end assembly 508 has as its purpose the mechanical objective of operating the tips 506 while at the same time providing an integrated active/shield embodiment generally corresponding to that of FIGS. 17-20 where the embodiment of FIGS. 17-20 is directed to non-articulable instruments while the embodiments of FIG. 27 and those described hereinafter are directed to articulable instruments.

The handle 510 generally comprises conventional technology; however, there are inventive features thereof which facilitate utilization of the integrated active/shield technology of the present invention.

An insulating sheath 517 disposed over front end assembly 508 may be attached to the outside thereof in such a manner that the position thereof with respect to assembly 508 can be adjusted in a longitudinal direction. Accordingly, more or less of the tips 506 can be exposed in accordance with the needs of the surgical application.

Figure 28:
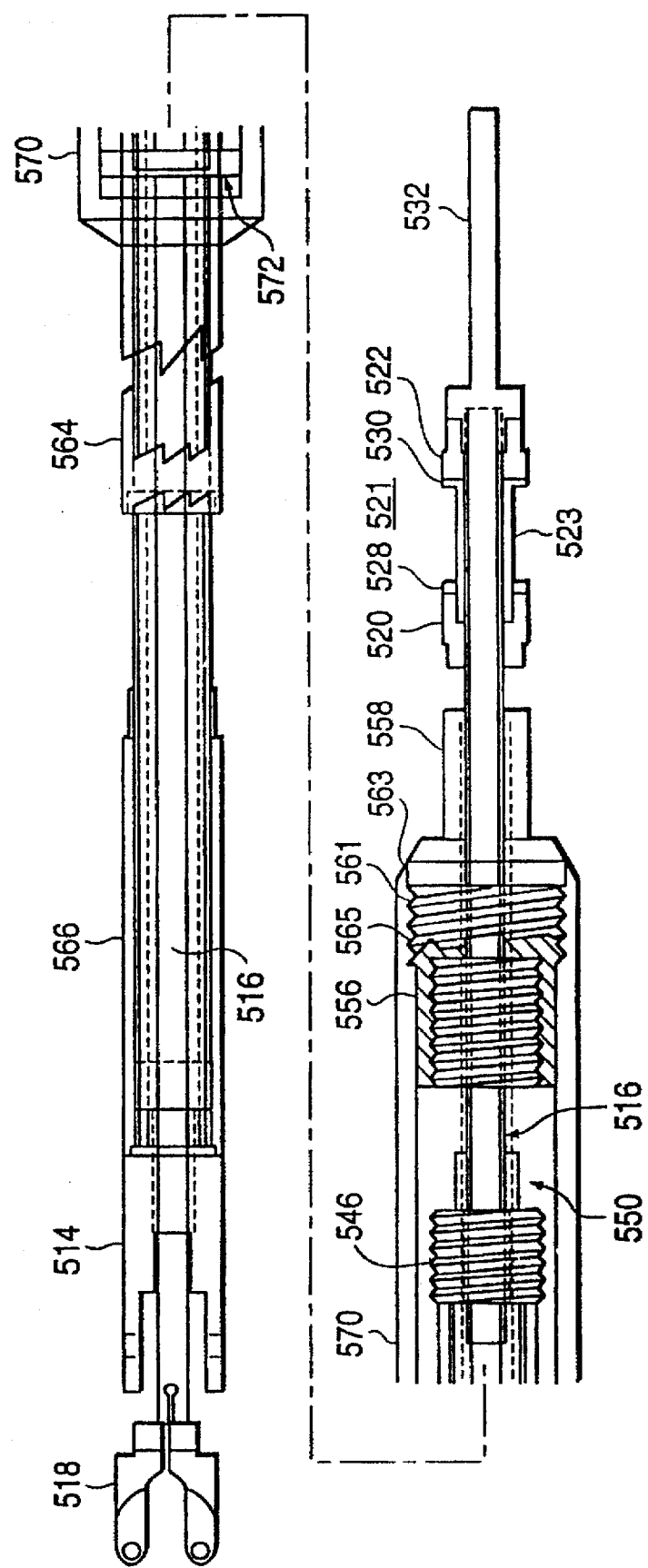
FIG. 28 is a partial schematic and partial cross-sectional view of a front end adaptor subassembly for use with the instrument of FIG. 27.
Figure 29:
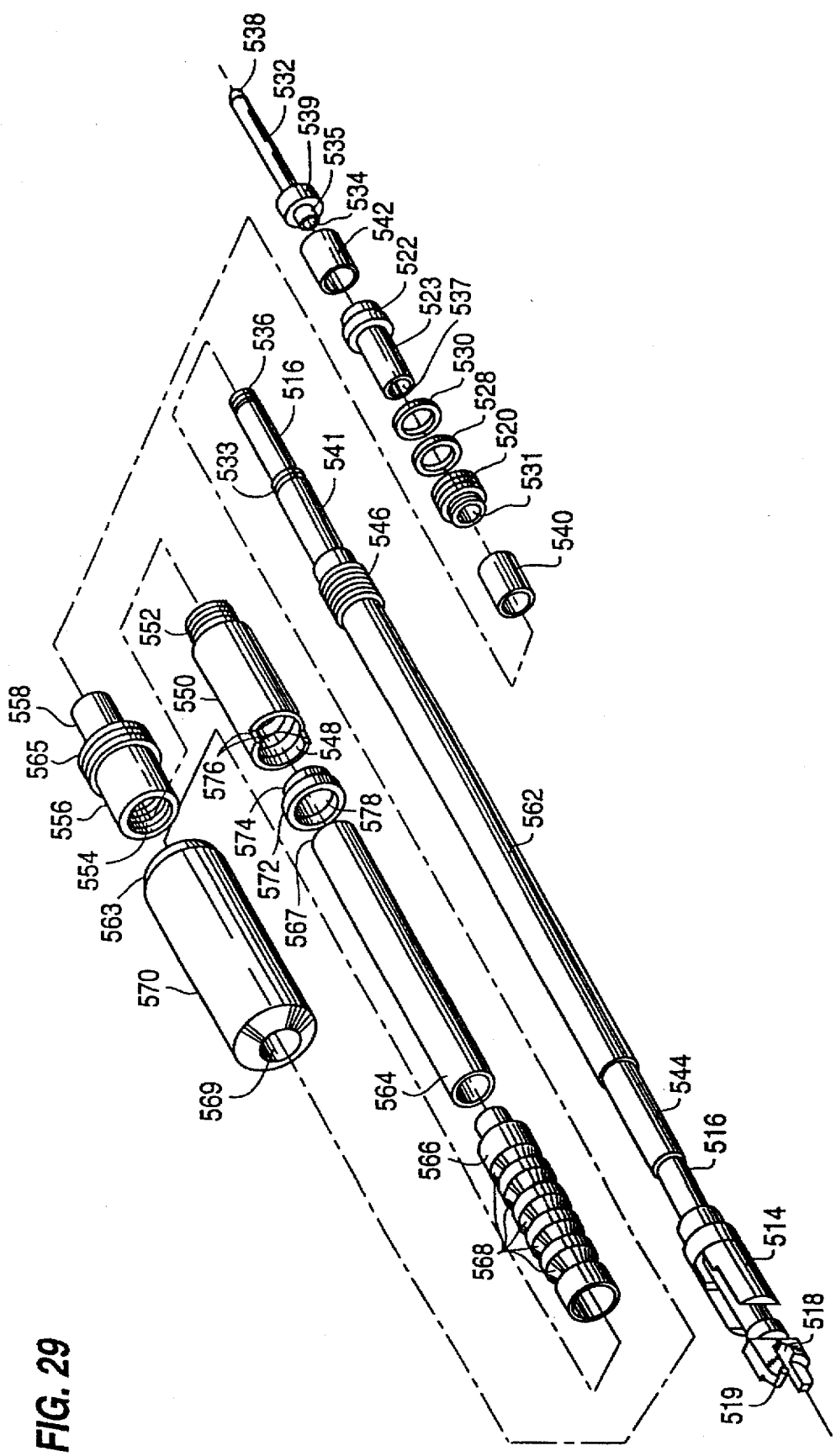
FIG. 29 is an exploded view of the illustrative front end assembly of FIG. 28.

Referring now to FIGS. 27, 28 and 29, the front end assembly 508 will be described in greater detail where this embodiment is identified for purposes of the present invention as a coupling design while another embodiment to be described hereafter is identified as a spacer design. In each of these designs, a front end assembly (508 in the case of coupling design) is employed which is typically about 30 centimeters in length. At the center of each is a driver rod 516, this being a conductive part which couples active current to the tips 506 and which also couples the mechanical forces which actuate the tips. The driver rod is connected at the distal end to a conventional driver 518 which is a conventional flexural metallic element having ends 519 which interface with the tips 506 and connect the tips mechanically to the instrument 500.

Near the proximal end of driver rod 516 is an insulated spool assembly 521 which comprises a front spool 520, a rear spool 522 and a pair of involute washers or cleavices 528 and 530 mounted on tubular portion 523 of the rear spool. A pair of ears 524 are attached to the upper end of trigger mechanism 526 where one of these ears is shown in FIG. 27.

The spool 520 includes a bore 531 having into which a ridge 533 formed on rod 516 is force fit to thereby couple spool 520 to the rod. In a similar manner ridge 535 on driver rod adaptor 532 is force fit into a bore 537 extending through rear spool 522 to couple the rear spool to the driver rod adaptor.

Insulation layer 542 extends over ridge 539 and extends over adaptor rod 532 approximately half way down the length thereof to insulate the driver rod adaptor from the handle. Moreover, similar insulation is provided by (a) insulation segment 541 which extends between a proximal point at ridge 533 (Note the insulation segment 541 has been cut back for ease of illustration in FIG. 29 as in the case with other layers in FIGS. 27-31.) and a distal point proximal to the proximal end of a tube adaptor 546 and (b) insulation layer 540 which extends over tubular portion 543 of rear spool 520 and insulation segment 541 to provide further insulation of the rod 516 with respect to the handle.

The trigger mechanism also includes conventional motion translating elements 526 which do not form part of the present invention. Latch 529 conventionally locks the trigger in a desired position so that the tissue can be continuously grasped.

In accordance with the present invention the spools 520 and 522 are made of insulating material such as ULTEM whereby forces from trigger 504 may be transmitted to driver rod 516 via spool assembly 521. In particular, as trigger 504 pivots about pin 527 during actuation, the ears 524 push on the stainless steel (for example) involute washers 528 and 530 to thereby provide uniform linear motion of driver rod 516. That is, the curvature of involute washers 528 and 530 and the curvature of the portions of ears 524 which coact with the washers are such that the curvilinear motion of the ears is translated to linear motion of the actuator rod 516. The metallic washers 528 also act as a buffer between the metallic ears 524 and the spools 520 and 522. That is, since the spools are made from insulating material they are not as well suited as the washers 528 and 530 to withstand engagement by the ears 524 over an extended period of time without deformation. Accordingly, the washers are interposed between the ears 524 and the spools 520 and 522.

In order to connect the actuator rod 516 to the receptacle 536 of the unitary connector, actuator rod adaptor 532 is provided at the distal end thereof with a threaded opening 534 into which is threaded the threaded proximal end 536 of actuator rod 516. Accordingly, it is the proximal end 538 of adaptor rod 532 which slides in the receptacle 536.

Typically the translational motion of actuator rod 516 may be about 0.068 inch during complete actuation of trigger 504 and thus as described hereinbefore with respect to the receptacle 436 of the unitary connector assembly 428 of FIG. 21, the length of receptacle 436 is such as to insure application of active electrode potential to actuator rod 516 during complete articulation of the instrument.

In accordance with a further feature of the invention, due to the provision of insulating spools 520 and 522, the trigger 504 is electrically insulated from the active potential applied to actuator rod 516. Moreover, in view of the active/shield technology described hereinbefore, the potential applied to handle 510 is at or near patient potential and thus the surgeon may safely grasp the handle without fear of electrical shock. This is in contradistinction to conventional electrosurgical instruments, as described hereinbefore, where the body of the instrument is at active potential while a thin insulating coating prevents conduction except at the active tip. As described hereinbefore, this insulating coating may become damaged and be the source of electrical shock to the surgeon. Hence, it can be seen that in the instruments of the present invention, state of the art mechanical features are provided while the electrical insulation is effectively turned inside out. That is, with the provision of the above-described active/shield technology and with the prevention of the insulating mechanical connection via spools 520 and 522 between the trigger 504 and the actuator rod 516, the body of handle 510 has maintained patient potential, there being no delicate insulation required to protect the surgeon's hands. Moreover, as described hereinbefore, if an insulation fault occurs such that shield 564 or handle body 510 is connected to active potential, the monitor circuitry 32 will effect a fail-safe condition.

Although not shown, the side surface of handle 510 are also provided with indentations 416 and ramps 420 as shown in FIG. 18 with respect to instrument body 414 whereby the shield monitoring contacts 440 may be engaged with the indentations 416 as shown in FIG. 24.

In some surgical applications, the clasping force generated at the tips 506 may be as much as 5 to 10 pounds which, due to lever action, may translate to several hundred pounds of longitudinal reaction forces. To absorb these forces, a tube 544 is provided which may be made of stainless steel or the like. The tube is provided with threaded tube adaptor 546 disposed at the approximate proximal end thereof and securely attached thereto. The threaded tube adaptor 546 is threaded into a internal threaded opening 548 of a coupling 550 where the coupling 550 is made of an insulating material such as ULTEM. The threaded proximal end 552 of coupling 550 is in turn threaded into the internal opening 554 of a front end adaptor 556 made of stainless steel or the like. A tubular portion 558 of adaptor 556 projects into an opening (not shown) in the distal end of handle 510, as shown in FIG. 27. As also shown in this figure, the tubular tip 558 is held in place within handle 510 by a set screw 560, which set screw prevents rotation and translation of the tubular tip 558 to thereby preventing rotation of the tips 506 at the distal end of the instrument.

Because the coupling 550 is made of an insulating material, the active potential applied to yoke 514 and tips 506 is not applied to the instrument handle 510. Thus, the tube 544, coupling 550 and the adaptor 556 absorb the large translational forces mentioned above due to the interconnection of these elements and the attachment of adaptor 566 to handle 510 as described above.

Disposed around tube 544 is insulating layer 562 which may be made of FEP or the like. Disposed around insulator layer 562 is sheath tube 564 made of stainless steel or the like which performs the shielding function of the present invention corresponding to the shield 400 of FIG. 17 to thus also perform a primary structural support function of the instrument. The shield 564 is not only insulated from the active potential by layer 562 but also by an insulating spacer 566 disposed between yoke 514 and the shield, the spacer typically comprising ULTEM. In accordance with a further aspect of the invention, the spacer 566 is provided with a plurality of grooves 568 which will be described in more detail hereinafter with respect to the sheath assembly 508.

The proximal end 567 of shield tube 564 extends through an opening 569 in the distal end of a sheath element 570 and is secured physically and electrically by welding or the like within an internal opening 578 of a conductive sheath adaptor 572 disposed within sheath element 570 as will be further described below. Accordingly, the sheath 570 is also maintained at or near patient potential of the shield tube 564. Moreover, as can be seen in FIG. 27, the sheath element 570 abuts the front end of handle 510 whereby handle 510 is also maintained at or near patient potential. In actuality, it should be noted that in fact it is the handle 510 that is maintained at shield potential due to coupling thereof to unitary connector 512 which in turn causes the sheath element 570 and the shield 564 to also be maintained at or near patient potential.

The coupler 550 and front end adaptor 556 are disposed within sheath 570. As stated above, conductive sheath adaptor 572 is also disposed therein where the adaptor is provided with ridges 574 which mate with ridges 576 at the distal end of adaptor 572 to further prevent rotation of the coupling 550 together with the set screw 560 of FIG. 27 as discussed above. The sheath 570 has internal threads 561 (See FIG. 28) at the proximal end 563 thereof whereby the sheath is threaded onto an external threaded portion 565 of front end adaptor 556. Thus, the sheath 570 may be threaded onto portion 565 to tightly fit the adaptor 572, the coupler 550, and the front end adaptor within the sheath. As indicated above, the internal opening 578 of adaptor 572 accommodates distal end 567 of shield 564 and this distal end may be secured by appropriate means within adaptor 572 to prevent rotation and provide conductivity thereof with respect to the adaptor.

Hence, it can now be seen how the front end assembly 508 of FIGS. 27–29 provides a capability of coupling not only mechanical forces from trigger 504 to tips 506 but also implements the integrated active/shield technology of the present invention.

It should be noted with respect to the foregoing coupling embodiment of the articulable instrument of the present invention that the sheath tube 564 and the spacer 566 do not bear any of the above-mentioned longitudinal forces which are generated within the front end assembly. As stated above, these are born by tube 544, coupling 550 and adaptor 556. This structure is particularly advantageous in that the substantial longitudinal forces can be readily absorbed by the foregoing elements.

In the following spacer embodiment of the invention to be described hereinafter, the spacer and shield both bear the above-mentioned longitudinal reactive forces and thus the number of parts required can be reduced. Moreover, the length of the instrument can somewhat be shortened since the sheath element 570 and the associated parts disposed therein are not required. However, an advantage of the coupling embodiment described hereinbefore is that it can readily absorb the large reactive longitudinal forces generated when large compressive forces are required at the tips 506.

Figure 30:
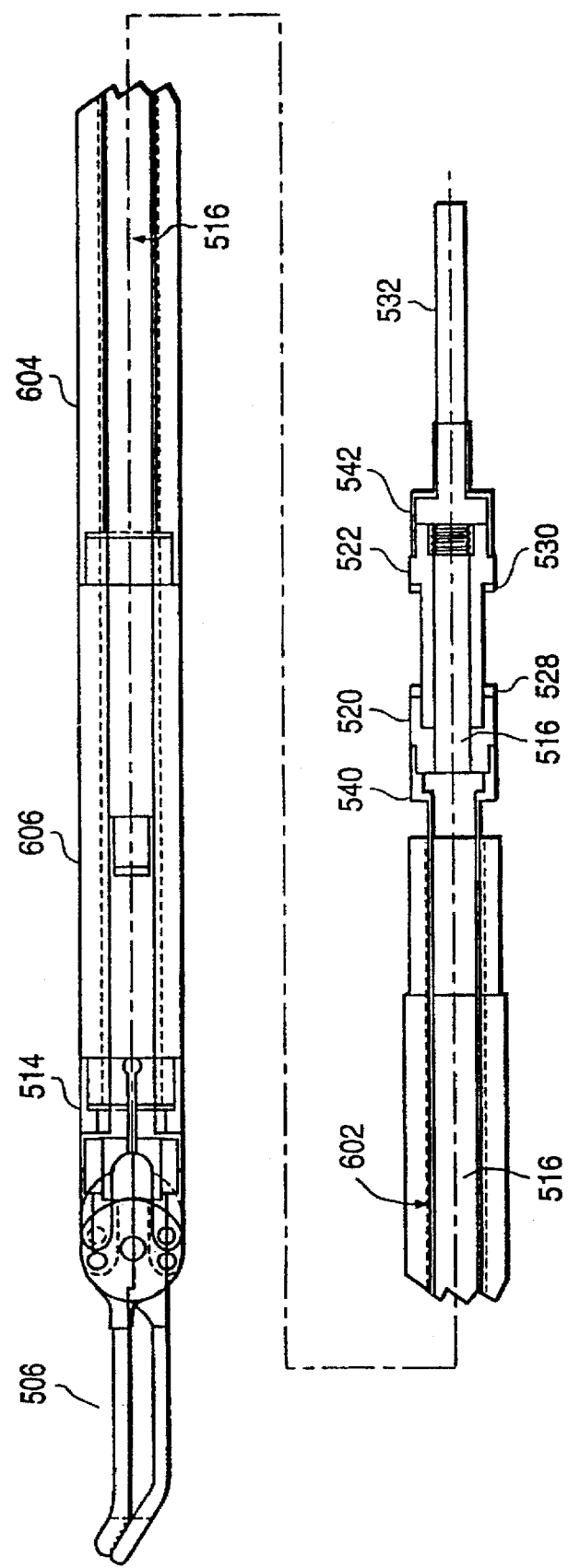
FIG. 30 is a schematic and partial cross-sectional view of a further embodiment of a front end assembly for use with articulable instruments in accordance with the present invention.
Figure 31:
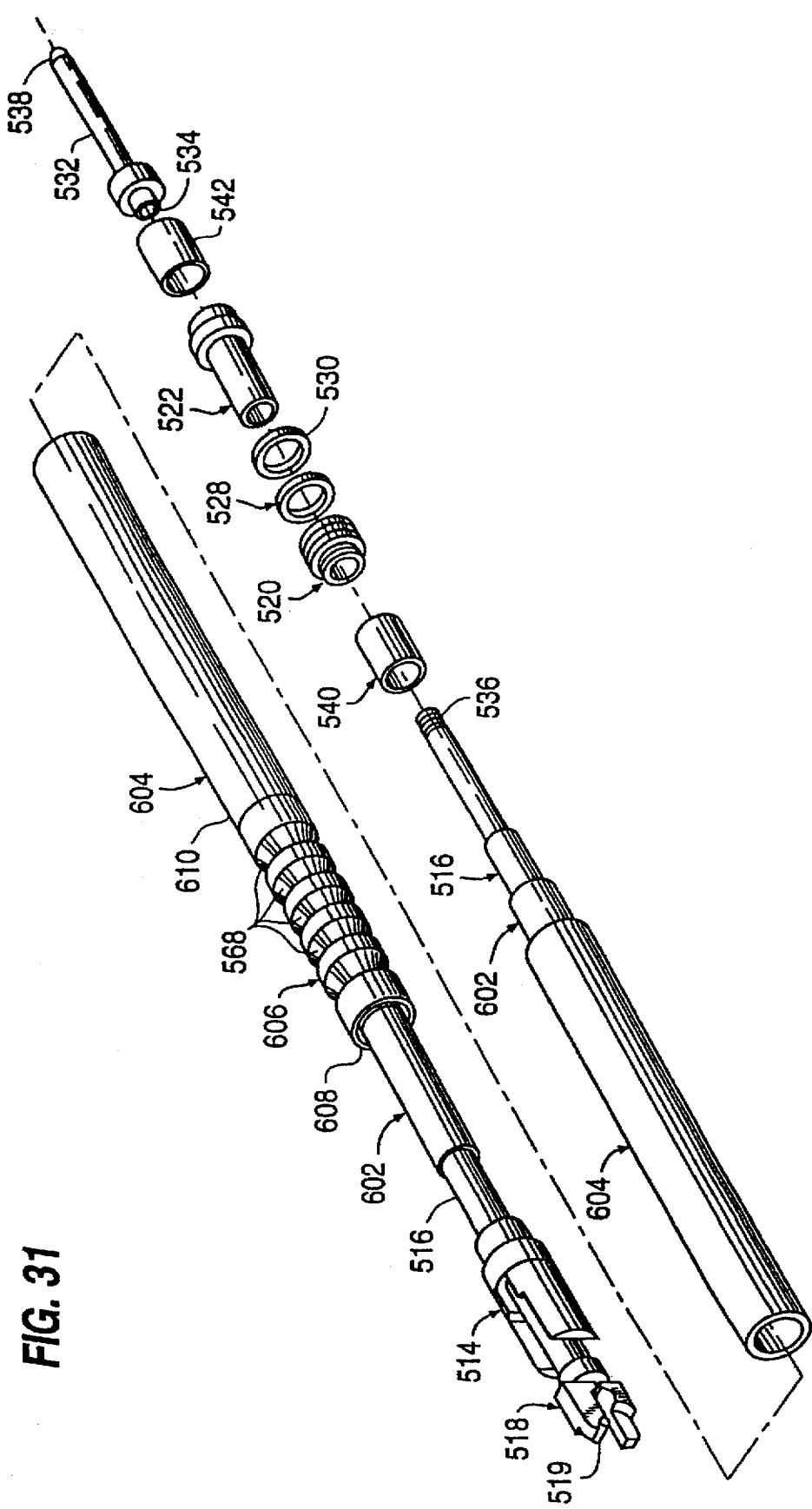
FIG. 31 is an exploded view of the front end subassembly of FIG. 30.

Reference should now be made to FIGS. 30 and 31 which illustrate the spacer design embodiment of a front end assembly in accordance with the present invention. In this embodiment, the driver rod 516 is at electrosurgical active potential. It is coated with insulation layer 602 and it slides within outer tube 604, which is the conductive part which provides the shielding function. Shield tube 604 may be held within the fixed portion of the handle 510 by a set screw 560, as shown in FIG. 27, to prevent rotation and translation thereof or by other known means. The shield tube 604 is separated from and insulated from the tips 506 and yoke 514, which are at active potential, by insulating spacer 606. The insulating spacer 606 and shield tube 604 bear the mechanical forces of actuation, which, as indicated above, can be up to 300 pounds. Accordingly, the joint 608 of the spacer with respect to yoke 514 and the joint 610 with respect to shield tube 604 becomes more critical in the spacer design embodiment since this spacer is made of an insulating material and has a relatively small diameter.

The remainder of the elements illustrated in FIGS. 30 and 31 correspond to those identified by a similar reference number in the heretofore described coupling design embodiment and perform the same function and thus description thereof is not repeated.

From the foregoing, it can be seen that the spacer embodiment of the front end assembly introduces less parasitic capacitance and requires less parts than the coupling design embodiment and thus where the anticipated clasping forces are not unusually excessive, this implementation is particularly advantageous. Of course, the strength of the insulating material can be also adjusted to accommodate excessive forces, if so desired. Moreover, the joints at 608 and 610 can be strengthened by employing known ceramic brazing techniques to affect brazing of the insulator tube 606 to yoke 414 at 608 and brazing of the tube to shield tube 604 at 610.

Figure 32:
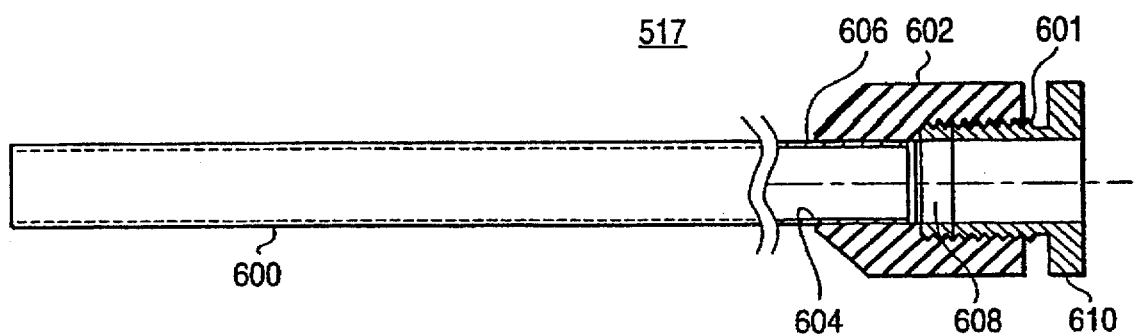
FIG. 32 is a cross-sectional view of an insulating sheath subassembly for use with the articulable instruments of FIGS. 27–31.

As can be seen in FIG. 27, an insulating sheath assembly 517 is disposed over shield tube 564 where the sheath assembly serves essentially the same purpose as the insulating layer 404 of FIG. 18. Moreover, sheath assembly 517 may be longitudinally adjustably disposed with respect to (a) shield tube 564 and insulating spacer 566 of the coupling design embodiment or (b) shield tube 604 and insulating spacer 606 of the spacer design embodiment where the insulating sheath assembly 517, as illustrated in FIG. 32, includes insulating tube 600 which is attached to a rigid insulating body 602. The tube 600 may be glued to the body at 604 to effect the permanent attachment or a detent 606 may be provided in body 602 whereby the insulating sheath 600 may be removably attached to the body 602. Disposed within threaded opening 601 in the body 602 is an elastic grommet 608 and threaded into opening 601 is a threaded lock control member 610 which engages the grommet to squeeze it and thus effect a tight fit between the grommet and the shield tube 564 of FIG. 29 or the shield tube 604 of FIG. 31. It can thus be seen that the insulating sheath assembly can be attached to the outside of the foregoing tubes so that it can be longitudinally positioned with respect therewith. This thus allows more or less of the tips 506 to be exposed in accordance with the needs of the surgical application.

The insulating tube 600 of the insulating sheath snugly fits over both the shield members 564 and 604 and the spacers 568 (FIG. 29) and 606 (FIG. 31). Because of the snug fit between the insulating tube 600 and the spacers 566 and 600, there is a tendency for moisture to be present therebetween due to capillary action. If this moisture were to reach the shield tube, a tendency for sparking would tend to occur which would possibly unduly heat the end of the instrument or, in an extreme ease, possibly trigger the shield monitor circuitry. To substantially eliminate this capillary action, the grooves 568 in spacers 566 and 606 are provided. In particular, these grooves widen the distance between the insulator tube 600 and the spacers 566 and 606 to thereby prevent further capillary action from occurring. A plurality of grooves 568 are provided in case the tip of the instrument is inserted into liquid prior to the procedure. However, if such insertion occurs, it will be only to a very limited degree since it would occur within the operative site. Accordingly, the first groove disposed above the level of the foregoing liquid will act to prevent further capillary action from occurring.

The outside diameter of the insulating tube 600 may be typically 8 millimeters or less and thus, when attached to the coupling design embodiment of FIGS. 27-29 or the spacer design embodiment of FIG. 30 and 31, may be readily inserted through a trocar cannula having an opening at least as small as 8 millimeters. Of course, these articulable instruments can also be inserted through cannulas having a 10 millimeter opening when an appropriately sized reducer is utilized.

What is claimed is:

1. Laparoscopic electrosurgical apparatus for use with an electrosurgical generator comprising:

a trocar cannula having a tubular passage for providing a conduit through a patient's skin to a peritoneal cavity of the patient, the trocar cannula having a proximal end and a distal end;

a tubular conductive shield having an inner surface and an outer surface and being removably insertable to an inserted position through the trocar cannula conduit, said shield having a distal end and a proximal end;

an active electrode probe having a tip and being adapted for connection to an electrosurgical generator and extending through the tubular conductive shield for effecting at the tip thereof an electrosurgical procedure within the peritoneal cavity where, when the tubular shield is in the inserted position thereof, the shield surrounds the active probe from at least (a) a proximal point prior to the distal end of the trocar cannula to (b) a distal point distal to the distal end of the trocar cannula and in proximity to the tip of the active probe;

at least one layer of electrical insulation disposed between the active probe and the inner surface of the tubular conductive shield;

an electrical terminal connected to the shield and adapted for connecting the shield to a reference potential;

whereby any abnormal condition which causes current to flow in said shield from said active probe is conducted to said reference potential to thus lessen a risk of patient injury; and monitor circuitry connected between said electrical terminal and said reference potential where the impedance between said electrical terminal and said reference potential is not more than about twenty ohms, said monitor circuitry being responsive to current in the shield to determine whether said abnormal condition exists.

2. An electrosurgical apparatus for use with an electrosurgical generator comprising:

a trocar cannula having a tubular passage for providing a conduit through a patient's skin where the trocar cannula has a proximal end and a distal end;

a tubular conductive shield having an inner surface and an outer surface and being removably insertable to an inserted position through the trocar cannula conduit, said shield having a distal end and a proximal end;

an active electrode probe having a tip and being adapted for connection to said electrosurgical generator and extending through the tubular conductive shield for effecting at the tip thereof an electrosurgical procedure within a patient's body where, when the tubular shield is in the inserted position thereof, the shield surrounds and is electrically insulated from the active probe from at least (a) a proximal point prior to the distal end of the trocar cannula to (b) a distal point distal to the distal end of the trocar cannula and in proximity to the tip of the active probe;

at least one layer of electrical insulation disposed between the active probe and the inner surface of the tubular conductive shield;

an electrical terminal connected to the shield and adapted for connecting the shield to a reference potential;

whereby any abnormal condition which causes current to flow in said shield from said active probe is conducted to said reference potential to thus lessen a risk of patient injury; and monitor circuitry connected between said electrical terminal and said reference potential where the impedance between said electrical terminal and said reference potential is not more than about twenty ohms, said monitor circuitry being responsive to current in the shield to determine whether said abnormal condition exists.

3. A safety shield system for use with a laparoscopic electrosurgical apparatus including a trocar cannula having a tubular passage for providing a conduit through a patient's skin to a peritoneal cavity of the patient, the trocar cannula having a proximal end and a distal end, an electrosurgical generator and an active electrode probe having a tip and being adapted for connection to said electrosurgical generator and extending through the trocar cannula for effecting at the tip thereof an electrosurgical procedure within the peritoneal cavity, said safety shield comprising a tubular conductive shield having an inner surface and an outer surface a distal end and a proximal end and being removably insertable to an inserted position through the trocar cannula, and where, when the tubular shield is in the inserted position thereof, the shield surrounds, and is electrically insulated from, the active probe from at least (a) a proximal point prior to the distal end of the trocar cannula to (b) a distal point distal to the distal end of the trocar cannula and in proximity to the tip of the active probe;

an electrical terminal connected to the shield and adapted for connecting the shield to a reference potential;

whereby any abnormal condition which causes current to flow in said shield from said active probe is conducted to said reference potential to thus lessen a risk of patient injury; and monitor circuitry connected between said electrical terminal and said reference potential where the impedance between said electrical terminal and said reference potential is not more than about twenty ohms, said monitor circuitry being responsive to current in the shield to determine whether said abnormal condition exists.

4. A safety shield system for use with an electrosurgical apparatus including a trocar cannula having a tubular passage for providing a conduit through a patient's skin where the trocar cannula has a proximal end and a distal end, an electrosurgical generator, and an active electrode probe having a tip and being adapted for connection to said electrosurgical generator and extending through the trocar cannula for effecting at the tip thereof an electrosurgical procedure, said safety shield comprising a tubular conductive shield having an inner surface and an outer surface a distal end and a proximal end and being removably insertable to an inserted position through the trocar cannula, and where, when the tubular shield is in the inserted position thereof, the shield surrounds, and is electrically insulated from, the active probe from at least (a) a proximal point prior to the distal end of the trocar cannula to (b) a distal point distal to the distal end of the trocar cannula and in proximity to the tip of the active probe;

an electrical terminal disposed on the shield and adapted for connecting the shield to a reference potential;

whereby any abnormal condition which causes current to flow in said shield from said active probe is conducted to said reference potential to thus lessen a risk of patient injury; and monitor circuitry connected between said electrical terminal and said reference potential where the impedance between said electrical terminal and said reference potential is not more than about twenty ohms, said monitor circuitry being responsive to current in the shield to determine whether said abnormal condition exists.

5. An electrosurgical apparatus for use with an electrosurgical generator comprising:

a handpiece having a tubular passage extending therethrough, the handpiece having a proximal end and a distal end;

a tubular conductive shield having an inner surface and an outer surface and extending at least partially through the handpiece passage, said shield having a distal end and a proximal end;

an active electrode probe having a tip and being adapted for connection to said electrosurgical generator and extending through the tubular conductive shield for effecting at the tip thereof an electrosurgical procedure where the shield surrounds the active probe from at least (a) a proximal point prior to the distal end of the handpiece to (b) a distal point distal to the distal end of the handpiece and in proximity to the tip of the active probe;

at least one layer of electrical insulation disposed between the active probe and the inner surface of the tubular conductive shield;

an electrical terminal connected to the shield and adapted for connecting the shield to a reference potential;

whereby any abnormal condition which causes current to flow in said shield from said active probe is conducted to said reference potential to thus lessen a risk of patient injury; and monitor circuitry connected between said electrical terminal and said reference potential where the impedance between said electrical terminal and said reference potential is not more than about twenty ohms, said monitor circuitry being responsive to current in the shield to determine whether said abnormal condition exists.

6. An electrosurgical apparatus for use with an electrosurgical generator comprising:

an outer member;

a tubular conductive shield having an inner surface and an outer surface and being mounted with respect to and extending at least partially through the outer member;

an active electrode probe having a tip and being adapted for connection to said electrosurgical generator and being mounted with respect to and extending through the tubular conductive shield for effecting at the tip thereof an electrosurgical procedure;

at least one layer of electrical insulation mounted between the active probe and the inner surface of the tubular conductive shield;

an electrical terminal connected to the shield and adapted for connecting the shield to a reference potential;

whereby any abnormal condition which causes current to flow in said shield from said active probe is conducted to said reference potential to thus lessen a risk of patient injury; and monitor circuitry connected between said electrical terminal and said reference potential where the impedance between said electrical terminal and said reference potential is not more than about 20 ohms, said monitor circuitry being responsive to current in the shield to determine whether said abnormal condition exists.

7. An electrosurgical apparatus for use with an electrosurgical generator comprising:

a tubular conductive shield having an inner surface and an outer surface;

an active electrode probe having a tip and being adapted for connection to said electrosurgical generator and being mounted with respect to and extending through the tubular conductive shield for effecting at the tip thereof an electrosurgical procedure;

at least one layer of electrical insulation mounted between the active probe and the inner surface of the tubular conductive shield;

an electrical terminal connected to the shield and adapted for connecting the shield to a reference potential;

whereby any abnormal condition which causes current to flow in said shield from said active probe is conducted to said reference potential to thus lessen a risk of patient injury; and monitor circuitry connected between said electrical terminal and said reference potential where the impedance between said electrical terminal and said reference potential is not more than about 20 ohms, said monitor circuitry being responsive to current in the shield to determine whether said abnormal condition exists.

8. An electrosurgical apparatus for use with an electrosurgical generator comprising:

an electrically conductive, outer member having an opening extending therethrough;

an active electrode probe having a tip and being adapted for connection to an electrosurgical generator and being mounted with respect to and extending at least partially through the outer member for effecting at the tip thereof an electrosurgical procedure;

at least one layer of electrical insulation mounted between the active probe and the outer member;

an electrical terminal connected to the outer member and for connecting the outer member to a reference potential;

whereby any abnormal condition which causes current to flow in said shield from said active probe is conducted to said reference potential to thus lessen a risk of patient injury; and monitor circuitry connected between said electrical terminal and the return lead of the electrosurgical generator where the impedance between said electrical terminal and said reference potential is not more than about 20 ohms, said monitor circuitry being responsive to current in the outer member to determine whether said abnormal condition exists.

9. Apparatus as in claims 6 or 7 where said one layer of insulation is mounted on said active probe.

10. Apparatus as in claims 6 or 7 where said one layer of insulation is mounted on the inner surface of said shield.

11. Apparatus as in claims 6 or 7 including at least two layers of insulation disposed between the active probe and the shield where one of the layers is mounted on the active probe and the other is mounted on the inner surface of the shield.

12. Apparatus as in claims 6 or 7 including alarm means responsive to the monitor circuitry to provide an indication of said abnormal condition.

13. Apparatus as in claims 6 or 7 including means responsive to the monitor circuitry for deactivating the electrosurgical generator in response to said abnormal condition being detected.

14. Apparatus as in claims 6 or 7 where said monitor circuitry includes circuitry for determining whether the amplitude of the shield current exceeds a predetermined threshold.

15. Apparatus as in claims 6 or 7 where said monitor circuitry includes circuitry for determining whether the ratio of the shield current to the current in the return lead to the electrosurgical generator exceeds a predetermined threshold.

16. Apparatus as in claims 6 or 7 where said monitor circuitry includes circuitry for determining whether a predetermined phase relationship exists between the shield current and the voltage applied to the active lead of the electrosurgical generator.

17. Apparatus as in claim 16 where said predetermined phase relationship is a substantially in phase relationship corresponding to said abnormal condition.

18. Apparatus as in claims 6 or 7 where said monitor circuitry includes spectral sensing circuitry responsive to at least one preselected frequency bandwidth of the shield current.

19. Apparatus as in claim 18 where said spectral sensing circuitry determines whether the amplitude of the electrical energy within said bandwidth exceeds a predetermined threshold.

20. Apparatus as in claim 18 where said frequency bandwidth is below the operating frequency of the electrosurgical generator.

21. Apparatus as in claim 20 where said bandwidth extends from about 50–250 KHz.

22. Apparatus as in claims 6 or 7 wherein said electrosurgical generator is disposed within a housing and where said monitor circuitry is disposed within said housing.

23. Apparatus as in claims 6 or 7 wherein said electrosurgical generator is disposed within a housing and where said monitor circuitry is disposed outside said housing.

24. Apparatus as in claim 23 including means for battery powering the monitor circuitry.

25. Apparatus as in claim 24 where said battery powering means includes means responsive to the flow of current in the shield to provide the battery power.

26. Apparatus as in claim 23 including adaptor means for connecting the monitor circuitry and the return electrode to the return terminal of the electrosurgical generator.

27. Apparatus as in claim 26 where said adaptor means includes sensing means for sensing whether a return electrode has been connected thereto and said monitor circuitry includes means responsive to the sensing means for at least providing an alert in response to the return electrode not being connected to the adaptor.

28. Apparatus as in claim 26 where said adaptor means includes sensing means for sensing whether the adaptor has been connected to the electrosurgical generator and said monitor circuitry includes means responsive to the sensing means for at least providing an alert in response to the adaptor not being connected to the generator.

29. Apparatus as in claims 6 or 7 where said monitor circuitry includes circuitry for determining whether a predetermined amount of shield current is present subsequent to the activation of the electrosurgical generator.

30. Apparatus as in claim 29 including means responsive to voltage applied to the active lead of the generator to sense said activation of the generator.

31. Apparatus as in claim 29 including means responsive to the current in the return lead to the generator to sense said activation of the generator.

32. Apparatus as in claims 6 or 7 including a shield-to-ground detection means for detecting whether the return electrode is connected to the electrosurgical generator including means for detecting whether the voltage on the tubular shield exceeds a predetermined threshold.

33. Apparatus as in claims 6 or 7 including means for latching the tubular conductive shield with respect to the active electrode to thereby provide the capability of adjusting the position of the distal end of the tubular conductive shield with respect to the distal end of the active electrode.

34. Apparatus as in claim 8 including alarm means responsive to the monitor circuitry to provide an indication of said abnormal condition.

35. Apparatus as in claim 8 including means responsive to the monitor circuitry for deactivating the electrosurgical generator in response to said abnormal condition being detected.

36. Apparatus as in claim 8 where said monitor circuitry includes circuitry for determining whether the amplitude of the shield current exceeds a predetermined threshold.

37. Apparatus as in claim 8 where said monitor circuitry includes circuitry for determining whether the ratio of the shield current to the current in the return lead to the electrosurgical generator exceeds a predetermined threshold.

38. Apparatus as in claim 8 where said monitor circuitry includes at least circuitry for determining whether a predetermined phase relationship exists between the shield current and the voltage applied to the active lead of the electrosurgical generator.

39. Apparatus as in claim 38 where said predetermined phase relationship is a substantially in phase relationship corresponding to said abnormal condition.

40. Apparatus as in claim 8 where said monitor circuitry includes spectral sensing circuitry responsive to at least one preselected frequency bandwidth of the shield current.

41. Apparatus as in claim 40 where said spectral sensing circuitry determines whether the amplitude of the electrical energy within said bandwidth exceeds a predetermined threshold.

42. Apparatus as in claim 40 where said frequency bandwidth is below the operating frequency of the electrosurgical generator.

43. Apparatus as in claim 42 where said bandwidth extends from about 50–250 KHz.

44. Apparatus as in claim 43 where said electrosurgical generator is disposed within a housing.

45. Apparatus as in claim 44 where said monitor circuitry is disposed within said housing.

46. Apparatus as in claim 44 where said monitor circuitry is disposed outside said housing.

47. Apparatus as in claim 46 including means for battery powering the monitor circuitry.

48. Apparatus as in claim 47 where said battery powering means includes means responsive to the flow of current in the shield to provide the battery power.

49. Apparatus as in claim 46 including adaptor means for connecting the monitor circuitry and the return electrode to the return terminal of the electrosurgical generator.

50. Apparatus as in claim 49 where said adaptor means includes sensing means for sensing whether a return electrode has been connected thereto and said monitor circuitry includes means responsive to the sensing means for at least providing an alert in response to the return electrode not being connected to the adaptor.

51. Apparatus as in claim 49 where said adaptor means includes sensing means for sensing whether the adaptor has been connected to the electrosurgical generator and said monitor circuitry includes means responsive to the sensing means for at least providing an alert in response to the adaptor not being connected to the generator.

52. Apparatus as in claim 8 where said monitor circuitry includes circuitry for determining whether a predetermined amount of shield current is present subsequent to the activation of the electrosurgical generator.

53. Apparatus as in claim 52 including means responsive to voltage applied to the active lead of the generator to sense said activation of the generator.

54. Apparatus as in claim 52 including means responsive to the current in the return lead to the generator to sense said activation of the generator.

55. Apparatus as in claim 8 including a shield-to-ground detection means for detecting whether the return electrode is connected to the electrosurgical generator including means for detecting whether the voltage on the tubular shield exceeds a predetermined threshold.

56. An electrosurgical apparatus as in claims 1, 2, 5, 6 or 7 where said tubular conductive shield has a layer of electrical insulation provided over at least a portion of an outer surface thereof.

57. A safety shield system as in claims 3 or 4 where said tubular conductive shield has a layer of electrical insulation provided over at least a portion of an outer surface thereof.

58. An electrosurgical apparatus as in claim 8 where said electrically conductive, outer member has a layer of electrical insulation provided over at least a portion of an outer surface thereof.

59. Apparatus as in claims 1, 2, 5, 6 or 7 where said electrosurgical generator includes a return lead and where said monitor is connected between said tubular conductive shield and said return lead.

60. A safety shield system as in claims 3 or 4 where said electrosurgical generator includes a return lead and where said monitor is connected between said tubular conductive shield and said return lead.

61. Apparatus as in claim 8 where said electrosurgical generator includes a return lead and where said monitor is connected between said electrically conductive, outer member and said return lead.

* * * * *